(12) United States Patent
Havel et al.

(10) Patent No.: US 11,317,892 B2
(45) Date of Patent: May 3, 2022

(54) OVER-THE-WIRE ULTRASOUND SYSTEM WITH TORQUE-CABLE DRIVEN ROTARY TRANSDUCER

(71) Applicant: Muffin Incorporated, West Lafayette, IN (US)

(72) Inventors: William J. Havel, West Lafayette, IN (US); Neal E. Fearnot, West Lafayette, IN (US); Sarah Robbins, Lafayette, IN (US); Yun Zhou, West Lafayette, IN (US); Peter S. McKinnis, Carrboro, NC (US); Marc C. Buhrmester, Dayton, IN (US)

(73) Assignee: Muffin Incorporated, West Lafayette, IN (US)

( * ) Notice: Subject to any disclaimer, the term of this patent is extended or adjusted under 35 U.S.C. 154(b) by 465 days.

(21) Appl. No.: 15/221,729

(22) Filed: Jul. 28, 2016

(65) Prior Publication Data
US 2017/0042508 A1 Feb. 16, 2017

Related U.S. Application Data

(60) Provisional application No. 62/203,983, filed on Aug. 12, 2015.

(51) Int. Cl.
*A61B 8/00* (2006.01)
*A61B 8/12* (2006.01)

(52) U.S. Cl.
CPC ............. *A61B 8/4466* (2013.01); *A61B 8/12* (2013.01); *A61B 8/445* (2013.01); *A61B 8/4461* (2013.01)

(58) Field of Classification Search
None
See application file for complete search history.

(56) References Cited

U.S. PATENT DOCUMENTS

| 2,790,095 A | 4/1957 | Peek et al. |
| 4,421,118 A | 12/1983 | Dow et al. |

(Continued)

FOREIGN PATENT DOCUMENTS

| CN | 1188401 | 7/1998 |
| EP | 1 977 230 A1 | 10/2008 |

(Continued)

OTHER PUBLICATIONS

U.S. Appl. No. 61/713,135 to Neal E. Fearnot et al., filed Oct. 12, 2012.

(Continued)

*Primary Examiner* — Jonathan Cwern
(74) *Attorney, Agent, or Firm* — Woodard Emhardt Henry Reeves & Wagner LLP

(57) ABSTRACT

Disclosed are embodiments of devices and methods for imaging the inside of a body part, such as a blood vessel. In particular embodiments, a catheter has a chamber within which is a transducer. A wire guide channel extends throughout the length of the catheter. The transducer is rotatable about the wire guide channel and the transducer is driven by a cable or other device that is connected to a motor which is located outside the catheter. In one form, a torque cable connects the transducer to the motor. In other embodiments, a pusher piece having a plurality of lumens is positioned in the catheter. Each of the lumens is sized to receive a cable, wire, and/or flushing fluid. The lumens maintain the orientation and separation of the cables, wires, and/or to flushing fluid.

14 Claims, 7 Drawing Sheets

(56) References Cited

U.S. PATENT DOCUMENTS

| | | | |
|---|---|---|---|
| 4,637,256 A | 1/1987 | Sugiyama et al. | |
| 4,720,266 A | 1/1988 | Leonard et al. | |
| 4,785,816 A | 11/1988 | Dow et al. | |
| 4,811,617 A | 3/1989 | Whiteman, Jr. | |
| 4,834,102 A | 5/1989 | Schwarzchild et al. | |
| 4,895,158 A * | 1/1990 | Kawabuchi | A61B 8/12 600/463 |
| 4,930,515 A | 6/1990 | Terwilliger | |
| 4,951,677 A | 8/1990 | Crowley et al. | |
| 4,972,839 A | 11/1990 | Angelsen | |
| 5,168,878 A | 12/1992 | Takano et al. | |
| 5,176,141 A | 1/1993 | Bom et al. | |
| 5,181,514 A | 1/1993 | Solomon et al. | |
| 5,237,884 A | 8/1993 | Seto | |
| 5,240,003 A | 8/1993 | Lancee et al. | |
| 5,373,845 A | 12/1994 | Gardineer et al. | |
| 5,377,682 A * | 1/1995 | Ueno | A61B 8/12 600/446 |
| 5,377,685 A | 1/1995 | Kazi et al. | |
| 5,437,283 A | 8/1995 | Ranalletta et al. | |
| 5,485,845 A | 1/1996 | Verdonk et al. | |
| 5,507,294 A | 4/1996 | Lum et al. | |
| 5,535,715 A | 7/1996 | Mouton | |
| 5,561,366 A | 10/1996 | Takahashi et al. | |
| 5,611,246 A | 3/1997 | Long et al. | |
| 5,651,366 A | 7/1997 | Llang et al. | |
| 5,701,901 A | 12/1997 | Lum et al. | |
| 5,729,508 A | 3/1998 | Baker et al. | |
| 5,799,655 A | 9/1998 | Jang et al. | |
| 5,846,204 A | 12/1998 | Solomon | |
| 5,865,751 A | 2/1999 | Yoshiyuki et al. | |
| 5,935,071 A | 8/1999 | Schneider et al. | |
| 5,951,480 A | 9/1999 | White et al. | |
| 6,162,178 A | 12/2000 | Garcia et al. | |
| 6,200,269 B1 | 3/2001 | Lin et al. | |
| 6,241,744 B1 | 6/2001 | Imran et al. | |
| 6,248,074 B1 | 6/2001 | Ohno et al. | |
| 6,354,814 B1 | 3/2002 | Kaufmann et al. | |
| 6,371,915 B1 | 4/2002 | Koger et al. | |
| 6,599,288 B2 | 7/2003 | Maguire et al. | |
| 6,607,502 B1 | 8/2003 | Maguire et al. | |
| 6,684,094 B1 | 1/2004 | Lehr et al. | |
| 6,689,066 B1 | 2/2004 | Masayoshi et al. | |
| 7,798,971 B2 | 9/2010 | Flesch et al. | |
| 8,206,307 B2 | 6/2012 | Barnard et al. | |
| 8,214,010 B2 | 7/2012 | Courtney et al. | |
| 2002/0062080 A1 | 5/2002 | Okawa et al. | |
| 2002/0082503 A1 | 6/2002 | Chandrasekaran et al. | |
| 2002/0087083 A1 | 7/2002 | Nix et al. | |
| 2002/0143252 A1 | 10/2002 | Dunne et al. | |
| 2003/0073907 A1 | 4/2003 | Taylor | |
| 2004/0133105 A1* | 7/2004 | Ostrovsky | A61B 5/06 600/437 |
| 2005/0027198 A1* | 2/2005 | Couvillon, Jr. | A61B 8/12 600/466 |
| 2005/0203416 A1 | 9/2005 | Angelsen et al. | |
| 2005/0283080 A1 | 12/2005 | Nita et al. | |
| 2006/0030797 A1 | 2/2006 | Zhou et al. | |
| 2006/0173348 A1 | 8/2006 | Wilser et al. | |
| 2006/0253023 A1 | 11/2006 | Lewis et al. | |
| 2007/0038110 A1 | 2/2007 | Flesch et al. | |
| 2007/0038114 A1 | 2/2007 | Couvillon, Jr. | |
| 2007/0149917 A1 | 6/2007 | Bennett et al. | |
| 2007/0167813 A1 | 7/2007 | Lee et al. | |
| 2007/0167821 A1 | 7/2007 | Lee et al. | |
| 2007/0239010 A1 | 10/2007 | Johnson | |
| 2008/0097403 A1 | 4/2008 | Donaldson et al. | |
| 2008/0161693 A1 | 7/2008 | Prager et al. | |
| 2008/0177138 A1 | 7/2008 | Courtney et al. | |
| 2008/0177183 A1 | 7/2008 | Courtney et al. | |
| 2008/0221506 A1 | 9/2008 | Rodriguez et al. | |
| 2008/0228081 A1 | 9/2008 | Becker et al. | |
| 2008/0234716 A1 | 9/2008 | Kiester | |
| 2008/0243035 A1 | 10/2008 | Crunkilton | |
| 2008/0319376 A1 | 12/2008 | Wilcox et al. | |
| 2009/0030312 A1 | 1/2009 | Hadjicostis | |
| 2009/0051121 A1 | 2/2009 | Sokek et al. | |
| 2009/0088631 A1 | 4/2009 | Dietz et al. | |
| 2009/0131798 A1 | 5/2009 | Minar et al. | |
| 2009/0156941 A1 | 6/2009 | Moore | |
| 2009/0306518 A1 | 12/2009 | Kurse et al. | |
| 2010/0036258 A1 | 2/2010 | Dietz et al. | |
| 2010/0145310 A1 | 6/2010 | Lee et al. | |
| 2010/0160788 A1 | 6/2010 | Davies et al. | |
| 2010/0168577 A1 | 7/2010 | Vezina | |
| 2010/0179426 A1 | 7/2010 | Davies et al. | |
| 2010/0217125 A1 | 8/2010 | Kadokura et al. | |
| 2010/0234736 A1 | 9/2010 | Corl | |
| 2010/0249599 A1 | 9/2010 | Hastings et al. | |
| 2010/0249601 A1 | 9/2010 | Courtney | |
| 2010/0249602 A1 | 9/2010 | Buckley et al. | |
| 2010/0249604 A1 | 9/2010 | Hastings et al. | |
| 2011/0021924 A1 | 1/2011 | Sethuraman et al. | |
| 2011/0021926 A1 | 1/2011 | Spencer et al. | |
| 2011/0071400 A1 | 3/2011 | Hastings et al. | |
| 2011/0071401 A1 | 3/2011 | Hastings et al. | |
| 2011/0166455 A1 | 7/2011 | Cully et al. | |
| 2011/0196286 A1 | 8/2011 | Robertson et al. | |
| 2011/0237955 A1 | 9/2011 | Dietz et al. | |
| 2011/0263986 A1 | 10/2011 | Park et al. | |
| 2011/0301508 A1 | 12/2011 | Sethuraman et al. | |
| 2012/0022379 A1 | 1/2012 | Gubbini et al. | |
| 2012/0108980 A1 | 5/2012 | Shilling et al. | |
| 2012/0172698 A1 | 7/2012 | Teo et al. | |
| 2012/0265070 A1 | 10/2012 | Sliwa et al. | |
| 2013/0066304 A1 | 3/2013 | Belson et al. | |
| 2013/0303907 A1 | 11/2013 | Corl | |
| 2013/0345556 A1 | 12/2013 | Courtney et al. | |
| 2014/0107489 A1 | 4/2014 | Fearnot et al. | |
| 2014/0107490 A1 | 4/2014 | Fearnot et al. | |
| 2014/0107491 A1 | 4/2014 | Fearnot et al. | |
| 2014/0107492 A1 | 4/2014 | Zhou | |
| 2014/0194743 A1 | 7/2014 | Havel et al. | |
| 2015/0094595 A1 | 4/2015 | Havel et al. | |
| 2015/0216503 A1 | 8/2015 | Fearnot et al. | |

FOREIGN PATENT DOCUMENTS

| | | |
|---|---|---|
| JP | H03215252 A | 9/1991 |
| JP | H05 154150 A | 6/1993 |
| JP | H05269133 A | 10/1993 |
| JP | 06-209939 A | 8/1994 |
| JP | 10-262974 A | 10/1998 |
| JP | 2000-126184 A | 5/2000 |
| JP | 2000-15754 A | 6/2000 |
| JP | 2001 046367 A | 2/2001 |
| JP | 2001-046375 A | 2/2001 |
| JP | 2002 034981 A | 2/2002 |
| JP | 2003 116853 A | 4/2003 |
| JP | 2003 339697 A | 12/2003 |
| JP | 2004/129697 | 4/2004 |
| JP | 2006 325875 A | 12/2006 |
| JP | 2007 000293 A | 1/2007 |
| JP | 2007-267998 A | 10/2007 |
| WO | WO 95/19143 A1 | 7/1995 |
| WO | WO 00/23125 A2 | 4/2000 |
| WO | WO 2012/061643 A1 | 5/2012 |
| WO | WO 2014/059292 A1 | 4/2014 |
| WO | WO 2014/059299 A1 | 4/2014 |
| WO | WO 2014/059315 A1 | 4/2014 |
| WO | WO 2015/050860 A1 | 4/2015 |

OTHER PUBLICATIONS

U.S. Appl. No. 61/713,142 to Neal E. Fearnot et al., filed Oct. 12, 2012.

U.S. Appl. No. 61/885,155 to William J. Havel et al, filed Oct. 1, 2013.

English Abstract of JP H05-154150 A, Feb. 28, 2017.

English Abstract of CN 1188401, dated Nov. 16, 2005.

International Patent Application PCT/US2016/046518 International Search Report and Written Opinion dated Nove. 8, 2016. 12 pages.

(56) References Cited

OTHER PUBLICATIONS

Office action, Chinese appln. 201380064735.4, dated Jul. 22, 2016, 15 pgs.
International Search Report and Written Opinion issued in PCT/US2013/064570, dated Jan. 24, 2014.
International Search Report and Written Opinion issued in PCT/US2013/064579, dated Jan. 23, 2014.
International Search Report and Written Ooinion issued in PCT/US2013/064606, dated Jan. 8, 2014.
International Search Report and Written Opinion issued in PCT/US2013/064611, dated Jan. 28, 2014.
International Search Report and Written Opinion issued in PCT/US2013/064618, dated Jan. 24, 2014.
International Search Report and Written Opinion issued in PCT/US2013/078245, dated Apr. 25, 2014.
International Search Report and Written Opinion issued in PCT/US2014/023088, dated Aug. 18, 2014, 14 pgs.
International Search Report and Written Opinion issued in PCT/US2014/023092, dated Aug. 12, 2014, 16 pgs.
International Search Report and Written Opinion issued in PCT/US2014/058289, dated Jan. 9, 2015, 17 pgs.

* cited by examiner

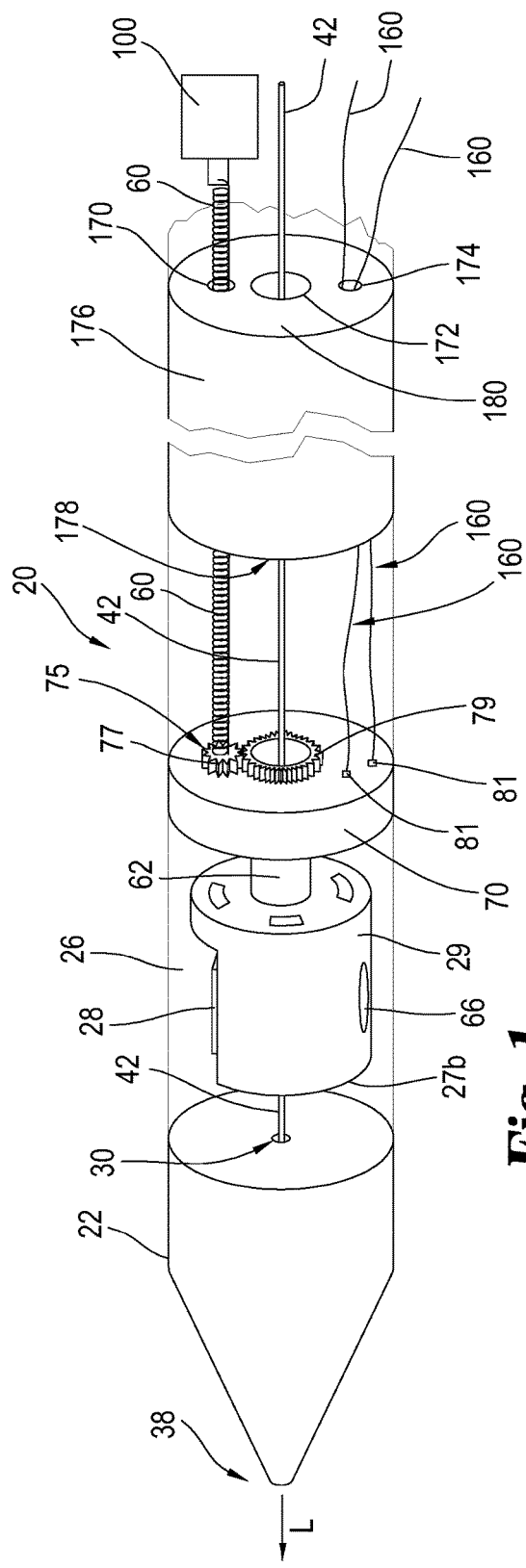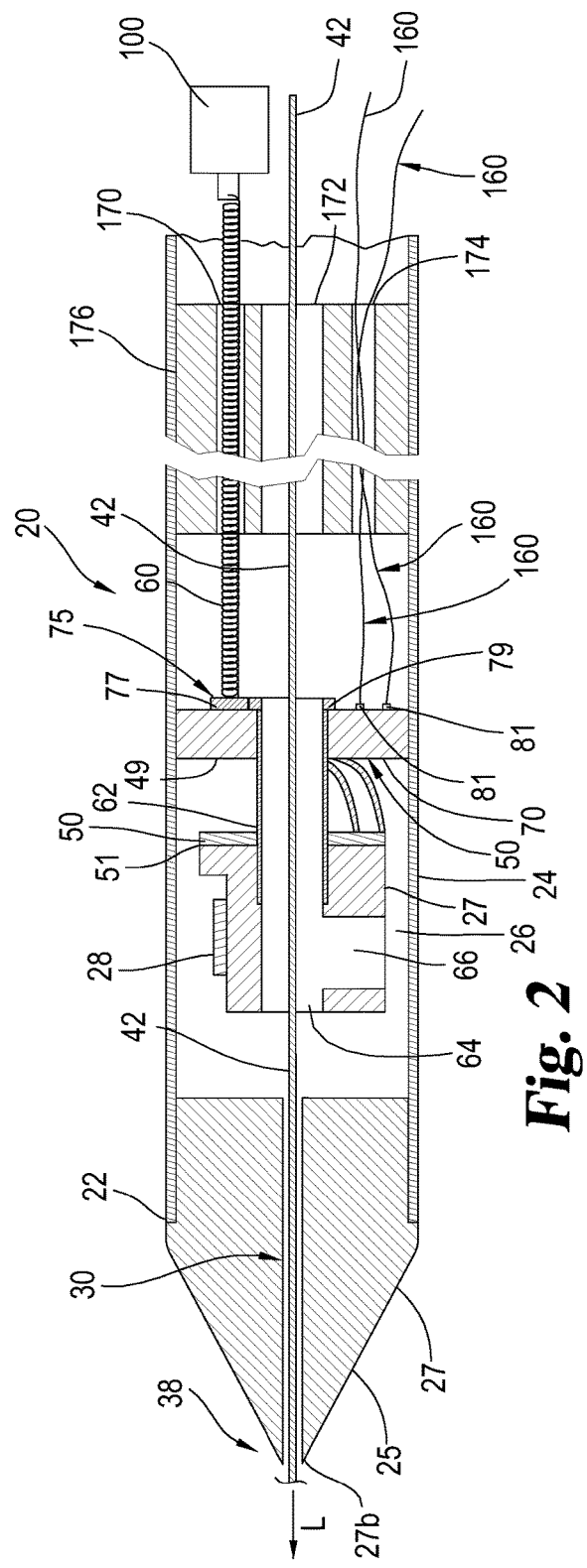

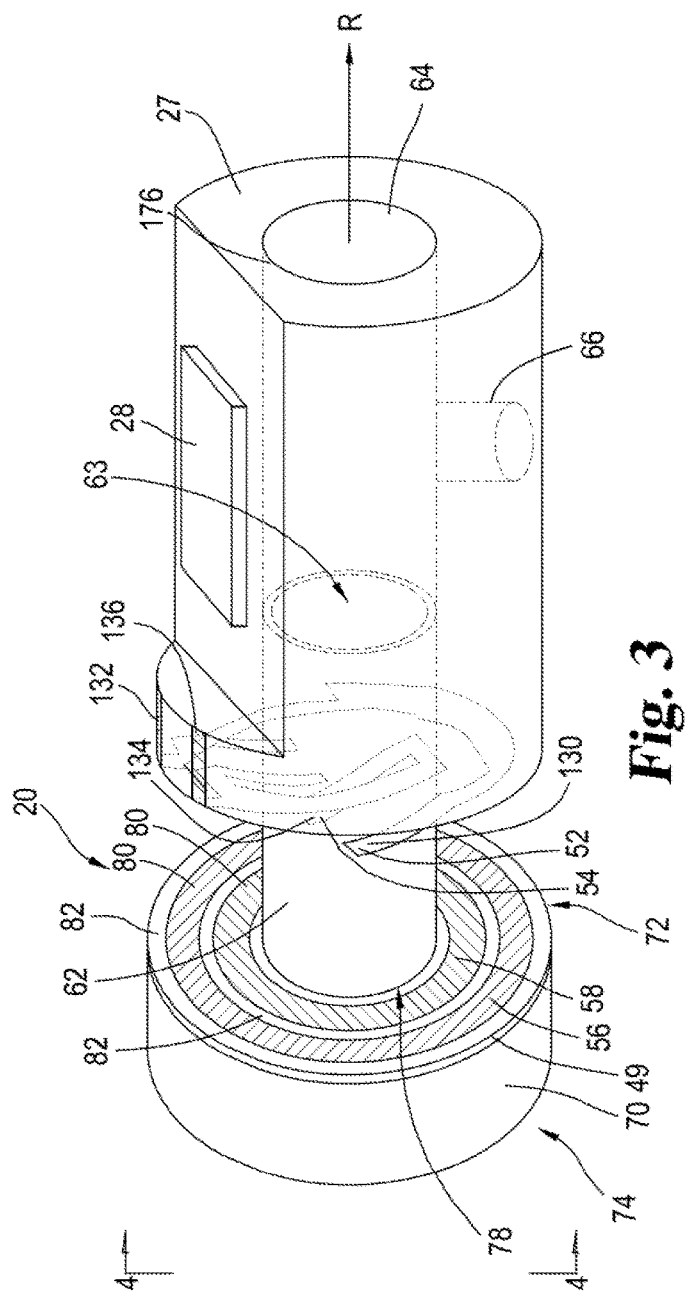
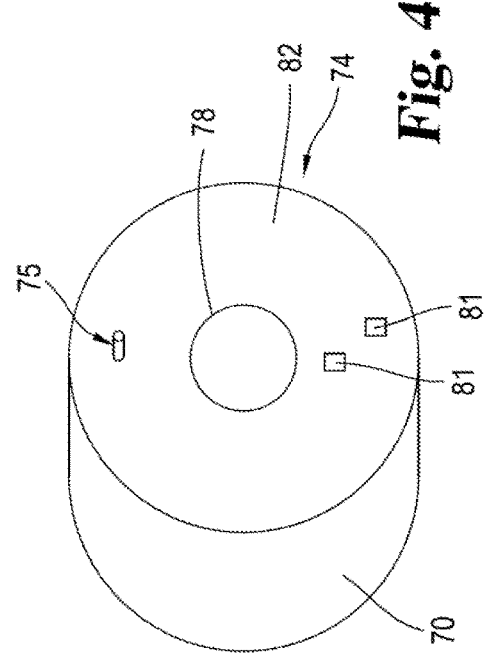

OVER-THE-WIRE ULTRASOUND SYSTEM WITH TORQUE-CABLE DRIVEN ROTARY TRANSDUCER

The present disclosure concerns devices and methods for ultrasound use within the human body.

CROSS REFERENCE TO RELATED APPLICATION

This application claims the benefit of U.S. Provisional Application No. 62/203,983 filed Aug. 12, 2015, which is herein incorporated by reference in its entirety.

BACKGROUND

Ultrasound technology has been used for therapeutic and diagnostic medical procedures, which can include providing imaging of internal portions of a body. For example, devices have been proposed for ultrasound imaging within blood vessels to view the condition of the vessel and/or placement or condition of a device placed in the vessel, as well as to help to determine plaque volume and the degree of stenosis within an artery lumen. That information is often difficult to obtain through angiographic imaging and exterior ultrasound imaging, particularly in regions having multiple overlapping arterial segments.

In some examples of intraluminal ultrasound procedures, a catheter is fitted with a transducer. A wire guide is positioned within a body conduit through use of angiography or ultrasound and is used to safely direct the catheter through the anatomy. The catheter is slid over the wire guide and positioned near the farthest end of the wire guide. The transducer transmits and/or receives ultrasound waves. When a transducer is placed within the body, commonly it is inside a protective envelope, such as a tube, catheter, or similar housing or enclosure. The material of such an envelope may be selected for its similarity in acoustic impedance to that of bodily fluids, so that there is little or no attenuation as ultrasound waves travel from that material to the fluids or tissues of the body. The inner pocket or volume of the body within which the transducer is placed needs a coupling medium having an acoustic impedance similar to that of the envelope material and the body's fluids to allow maximum transmission. Without such medium, transmission of the ultrasound waves may be significantly impeded. Suitable coupling media include biocompatible fluids such as saline, certain oils, alcohols, and other fluids.

Of course, some coupling media (e.g. saline) can be corrosive over time, particularly of metallic materials. If a corrosive coupling medium is to be used, a drawback is that degradation of part(s) of the transducer or other aspects of the device (e.g. structure used to turn or move the transducer) may occur. An unacceptably short shelf life for the product may thus result with such medium. Thus, the relatively low-cost medium of saline has significant downside to a practical internal transducer product.

Embodiments of internal transducer products using piezoelectric motors to turn or otherwise move a transducer have also been suggested. Applicable piezoelectric motors generally need dry conditions to operate, as they require a high friction contact area between a stator and a clutch. If fluid touches that contact area or interface, the friction will be substantially reduced, thereby also reducing the torque output of the motor. Accordingly, in such embodiments to prevent fluid from contacting the motor, a seal is included between the motor and the transducer to prevent leakage of the coupling medium from the volume around the transducer toward the motor. Such seals can fail over time, which is one potential factor in shelf life for such products.

Further difficulties arise in constructing adequate catheters having transducers in very small sizes in order to safely reach particular body conduits, such as for example with intravascular applications. Problems with existing two dimensional designs include wire guide channels which block a portion of the acoustic window. Additionally, wire guide channels take up valuable space in the catheter that could otherwise be used by ultrasound hardware.

Other problems exist in current catheter configurations. For example, in many cases in order to visualize the entirety of a significant length within the body (e.g. surfaces or portions of tissue, or of devices), the device must be moved along that length, with respective images of cross sections taken at particular locations. Such movement may be inexact, slow, result in distorted images, and the images are not provided in real time. Additionally, existing devices do not provide imaging information to aid in insertion of the catheter and can thus include risks associated with blind insertion.

Three-dimensional information provides the added value that it can be used to help in navigation and confirmation of position of devices within body conduits. In an intravascular example, catheters can be pulled back within vessels at a controlled speed and the image data obtained via ultrasound can be processed in order to create three-dimensional information. However, the catheter tip motion and angle must be known in order to produce accurate and usable data. Three-dimensional images may be acquired by one-dimensional arrays connected to a mechanical actuator which moves the arrays within the catheter or other device. Such designs are often expensive.

There remains a need for a catheter positionable over a wire guide which can provide accurate and efficient preparation and application of ultrasound, including efficient fluid injection means. There also remains a need for such a device that can view a medical device and one or more tissues or tissue parts simultaneously, particularly in cases in which the device and tissue(s) could not have been imaged reliably in any two-dimensional plane.

SUMMARY

Among other things, there are disclosed embodiments of devices for medical ultrasound application within a patient, and methods for making and using them. For example, a device for medical ultrasound in particular embodiments includes a housing having a longitudinal axis, a transducer configured for transmitting and/or receiving ultrasound signals and operatively coupled with a drive shaft extending substantially along the longitudinal axis wherein the transducer and the drive shaft positioned within the housing and the transducer rotates about the longitudinal axis in response to rotation of the drive shaft. Also included in this embodiment is a non-rotating wire guide positioned along the longitudinal axis within the housing and a torque cable offset a distance from the longitudinal axis, the torque cable operably connected to the drive shaft and a motor so that the drive shaft rotates in response to the torque cable. Optionally, a first gear is operably connected to the torque cable and a second gear is operably connected to the drive shaft, wherein the second gear is configured to interact with the first gear such that the second gear is configured to rotate when the first gear rotates. Optionally, in this particular embodiment, the first gear has a rotational axis offset from the longitudinal axis and the first gear is configured to rotate about the rotational axis and the second gear is configured to rotate about the longitudinal axis when the first gear rotates. In any embodiment, the device includes a mounting piece positioned within the housing, the mounting piece is configured to receive the transducer and the drive shaft, wherein the mounting piece defines a lumen that aligns with the longitudinal axis and is sized to receive the wire guide such that the wire guide is non-rotatable, and the mounting piece is configured to rotate about the longitudinal axis. Optionally in this embodiment, the device includes a slip ring assembly operably connected to the mounting piece and the torque cable. In some embodiments, the mounting piece defines a bore that extends along the longitudinal axis, and the slip ring assembly includes a stationary mount piece configured to retain the drive shaft sized to operatively mate with the bore. In any embodiment, the device includes a pusher piece operably connected to the housing, the pusher piece defining a plurality of lumens that span the length of the pusher piece wherein one of the plurality of lumens is sized to receive the wire guide and another of the plurality of lumens is sized to receive the torque cable. In this embodiment, optionally, another of the plurality of lumens of the pusher piece is sized to receive one or more transducer electrical wires operably connected to the transducer. In any embodiment, the housing is a catheter.

As another example a medical ultrasound device includes a housing having a longitudinal axis, a transducer positioned within the housing wherein the transducer is configured for transmitting and/or receiving ultrasound signals, and a mounting piece positioned within the housing and operatively coupled with a torque cable that is configured to rotate the mounting piece about the longitudinal axis. The mounting piece is also configured to receive the transducer, wherein the mounting piece defines a lumen that aligns with the longitudinal. Also included is a torque cable operably connected to the mounting piece to transmit torque to the mounting piece.

Optionally the device can include a non-rotating wire guide positioned within the housing along the longitudinal axis and a gear assembly positioned within the housing, the gear assembly having a first gear interactively coupled to a second gear, wherein the first gear is rotatably mounted to a stationary mount piece within the housing and the first gear is operatively connected to the torque cable, and the second gear is rotatably mounted to the stationary mount piece about the longitudinal axis. In some embodiments, the mounting piece defines a lumen sized to receive the wire guide. Other embodiments the device includes a second torque cable operably connected to the transducer, the first torque cable and the second torque cable configured to pivot and to rotate the transducer. In other embodiments the device includes a pusher piece operably connected to the housing, the pusher piece defining a plurality of lumens that span the length of the pusher piece wherein one of the plurality of lumens is sized to receive the wire guide and a second of the plurality of lumens is sized to receive the torque cable. Further in this embodiment, the lumen sized to receive the wire guide can include an ultrasound-transmissive fluid. In any embodiment, the device includes a motor positioned exteriorly to the housing, wherein the motor is operably connected to the torque cable.

Optionally the device includes a motor positioned exteriorly to the housing and a gear assembly mounted on the motor, wherein the torque cable is operably connected to the gear assembly and the torque cable is further configured to receive the wire guide therein. In some embodiments, the torque cable is offset a distance from the longitudinal axis. In any embodiment of the device, the transducer can be operatively coupled with a drive shaft extending substantially along the longitudinal axis such that the transducer and the drive shaft are positioned within the housing and the transducer rotates about the longitudinal axis in response to rotation of the drive shaft.

In yet another embodiment of a medical ultrasound device, the device includes a housing having a longitudinal axis, a non-rotating wire guide positioned within the housing along the longitudinal axis, a transducer positioned within the housing wherein the transducer is configured for transmitting and/or receiving ultrasound signals. The device also includes a mounting piece positioned within the housing and operatively coupled with a torque cable that is configured to rotate the mounting piece about the longitudinal axis, the mounting piece also configured to receive the transducer, wherein the mounting piece defines a lumen that is sized to receive the wire guide. The device further includes a torque cable operably connected to the mounting piece to transmit torque to the mounting piece, the torque cable further configured to receive the wire guide therein and a gear assembly mounted on a motor exterior to the housing, wherein the torque cable is also operably connected to the gear assembly.

Further forms, objects, features, aspects, benefits, advantages, and embodiments of the present invention will become apparent from a detailed description and drawings provided herewith.

BRIEF DESCRIPTION OF THE DRAWINGS

FIG. 1 is an illustrative perspective view of an embodiment of an ultrasound device in a disassembled configuration.

FIG. 2 is an illustrative cross-sectional view of the ultrasound device of FIG. 1.

FIG. 3 is an illustrative perspective view of a slip ring assembly of the ultrasound device of FIG. 1.

FIG. 4 is an illustrative perspective view of a stationary component of the FIG. 3 embodiment.

DESCRIPTION OF THE SELECTED EMBODIMENTS

Figure 6:
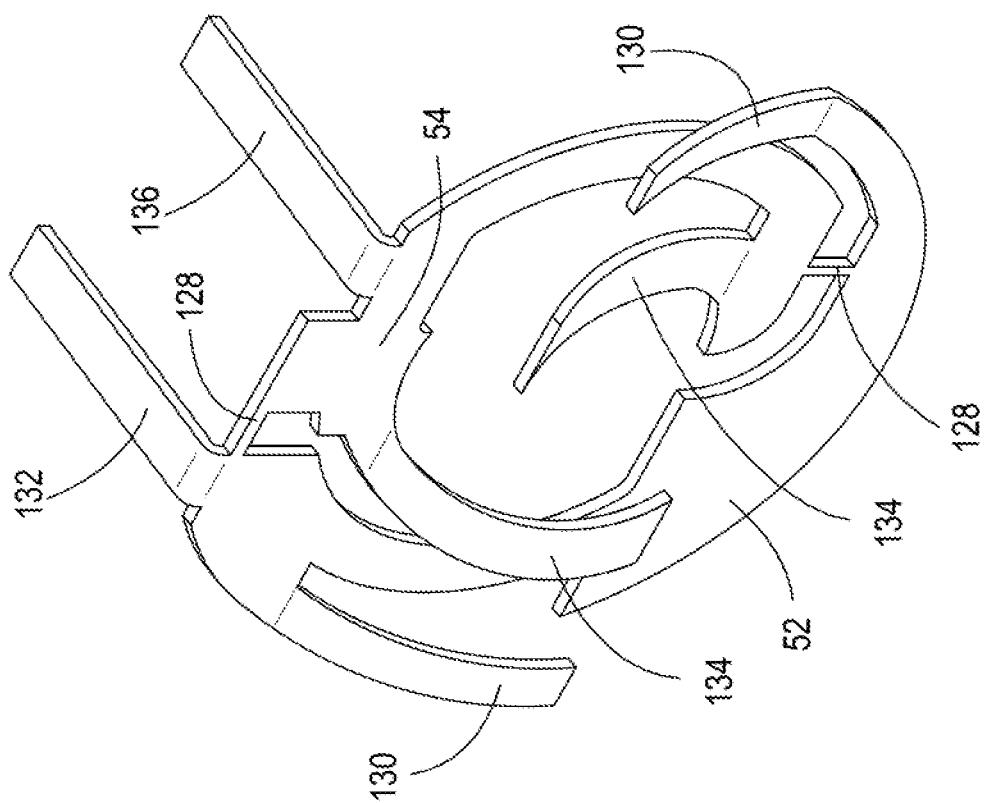
FIG. 6 is an illustrative perspective view of the rotational contact portion of FIG. 5.

For the purpose of promoting an understanding of the principles of the disclosure, reference will now be made to the embodiments illustrated in the drawings and specific language will be used to describe the same. It will nevertheless be understood that no limitation of the scope of the claims is thereby intended. Any alterations and further modifications in the described embodiments, and any further applications of the principles of the disclosure as described herein are contemplated as would normally occur to one skilled in the art to which the invention relates. Embodiments are shown in great detail, although it will be apparent to those skilled in the relevant art that some features that are not relevant to the present disclosure may not be shown for the sake of clarity.

Referring now generally to the drawings, shown are exemplary embodiments of a device 20 for internal ultrasound procedures. Such devices may be diagnostic or therapeutic (including interventional) in application, and include devices inserted percutaneously, subcutaneously or endoluminally into the patient. Device 20 can be used with a system which includes a console (not shown) for processing data or signals received from an ultrasound transducer. The ultrasound console can be a type which is generally used for medical ultrasonic imaging, e.g. generally including control devices usable by a physician and a graphic display which displays graphical images obtained during an ultrasound procedure. The device 20 is connectable to the console portion through standard connections. Device 20 can be used for obtaining images at various locations and conduits of a body such as a blood vessel, urethra, ureter, vagina, rectum, throat, ear, or through an artificial tract by percutaneous puncture for example. Device 20 is capable of transmitting and receiving ultrasound signals and then communicating data obtained from ultrasound signals to the console.

In the embodiment shown schematically in FIGS. 1 and 2, device 20 is shown in a disassembled configuration in which elements are illustrated with some distance between two elements. In an assembled configuration such that device 20 could be implanted in a patient's body, adjacent elements of device 20 will be positioned in contact with each other, as described in more detail below. In the embodiment shown schematically in FIGS. 1, 2, and 3, device 20 includes a catheter 22 or other flexible elongated or tubular member having a wall 24 and extending along a longitudinal axis L and a catheter tip 25 (or other tubular member) having a channel 30 and extending along the longitudinal axis L. Wall 24 has an inner surface defining an internal chamber 26, within which is included a mounting piece 29 housing a transducer 28 for sending and/or receiving ultrasound signals. Alternatively, catheter tip 25 may have a port or other feature to allow injection of fluid into internal chamber 26. The catheter tip 25 includes a channel or through hole 30 configured to receive a wire guide 42.

In the illustrated embodiments, the rotation axis R about which the transducer 28 rotates is aligned or coincides with the longitudinal axis L along catheter 22. In optional embodiments, transducer 28 may also be pivoted about a pivot axis substantially transverse or perpendicular to the rotation axis R, allowing ultrasound emission to extend forward (axially relative to the rotation axis) and laterally (radially relative to the rotation axis). Therefore, transducer 28 is capable of transmitting and receiving ultrasound signals in a variety of directions or orientations which are passed along data signal communication lines between transducer 28 and the ultrasound console.

Catheter 22 in the illustrated embodiment is an elongated device of plastic or other sturdy flexible material. In typical embodiments, catheter 22 is sized and configured for insertion into and/or travel along bodily orifices or lumens. Catheter 22 includes a control end which during use is nearest to the user and an application end which during use is nearest to the user's point of interest within the patient. The terms "control" and "application" are used throughout this description to describe these positional orientations. Wall 24 surrounds chamber 26, which is near the application end of device 20 in the illustrated embodiment. The application end of wall 24 is sized and configured to receive and retain catheter tip 25. The control end of wall 24 and/or catheter 22 may extend outside of the patient during use, or may attach to another piece that extends outside the patient, and may end in a handle or other operating portion for maneuvering catheter 22. The application side end of catheter tip 25 is tapered in some embodiments, and in the particular illustrated embodiment is open at end 38 to an external area surrounding the catheter. The application end of the catheter 22 is at least partially constructed of a material which has acoustic impedances similar to that of body fluids such as blood. Only the distal or control end of the catheter needs to be acoustically transparent, but more or all of catheter 22 may be made of the same material as wall 24 in some embodiments. Possible materials could include, for example, a polymer material such as polyethylene (PE), polymethylpentene (PMP), or acrylonitrile butadiene styrene (ABS).

Transducer 28 is indicated schematically in the drawings. The term "transducer" should be understood to include an assembly of two or more parts as well as a single piece. Embodiments of transducer 28 may be capable in particular examples of sending and receiving ultrasound waves in a range of frequencies which are typically used in medical ultrasound procedures, such as, for example, in the range from 20 kHz to 100 MHz. Transducer 28 is operably linked to a motor 100 via a torque cable 60 to permit transducer 28 to turn, pivot, or otherwise move. It will further be understood that "transducer" as used herein includes devices that transmit ultrasound signals (i.e. transform an electrical (RF) signal to ultrasound), receive ultrasound signals (i.e. transform ultrasound to an electrical (RF) signal), or both. Transmission of ultrasound may occur at one element of transducer 28 and reception at another element of transducer 28. Transducer(s) as described herein may have one or more piezoelectric elements as respective transducers, and may operate in combination with other transducers within or outside the body. As examples, "transducer" as used herein includes a split single element transducer on a rotating and/or pivoting member, a single element transducer on a rotating and/or pivoting member, or a one-dimensional array of elements on a rotating and/or pivoting member.

Channel 30 extends from the control end to the application end of the catheter 22. In the illustrated embodiment, channel 30 ends at the application side 27b of catheter tip 25. The channel 30 can be configured to accept varied sizes of wire guides, such as wire guides with diameters between 0.014" to 0.038". Channel 30 is sized and configured to permit effective injection and travel of a coupling medium toward chamber 26. In certain embodiments, mounting piece 29 defines at least one passageway 66 extending from channel 30 to chamber 26, such as the illustrated passageway 66, which is configured to permit the transfer of coupling medium into chamber 26. As illustrated, the passageway 66 is in open communication with chamber 26. In other embodiments, there may be greater or fewer than the one illustrated passageway defined in mounting piece 29. During rotation of the mounting piece 29 about the rotation axis R, coupling medium traveling within channel 30 toward the application end of catheter 22 will be pumped centrifugally through the passageway 66 and the surrounding chamber 26. In this way, acoustic matching can be achieved between body fluids, catheter 22, and the medium immediately surrounding transducer 28. Acoustic matching ensures that minimal signal losses occur when transmitting and receiving ultrasound signals between transducer 28 and body tissue which enhances the clarity of the resulting image.

As illustrated, passageway 66 may be perpendicular to a bore 64 or the passageway 66 may be angled with respect to the channel 30 (axially with respect to rotation axis R), such that the passageway extends from the channel 30 to the chamber 26 in a direction generally from the control end to the application end of the catheter 22. Moreover, it should be appreciated that the passageway(s) may be oriented differently than as illustrated.

Open end 38 of device 20 allows gas to move from chamber 26 to the external area outside of device 20 during filling or charging of chamber 26 with coupling medium. In an alternate embodiment, a dedicated exhaust port may be incorporated into the device and open end 38 may be absent. In certain embodiments, wherein the channel 30 is flushed during use of the catheter 22, an amount of gas(es) or liquid(s) may enter through open end 38 from the external area outside of the device 20 during insertion and/or use of the device 20, although the amount may be minimal, insubstantial or inconsequential to the use and operation of the device 20. As previously noted, in particular embodiments the diameter of the opening in end 38 is slightly smaller than channel 30.

Device 20 includes a slip ring assembly 50 and a hollow shaft 62 with the mounting piece 29 attached thereto as illustrated in FIG. 2. As can be appreciated there can be other arrangements between the mounting piece 29 and the hollow shaft 62 such as monolithic or separate attachable elements. Electronic signals pass between an ultrasound console and transducer 28 through both a stationary portion 49 and a rotating portion 51 which together form a slip ring assembly 50. A motor 100 is operatively connected with the shaft 62 or the mounting piece 29 while the rotating portion 51 of the slip ring assembly 50 is operatively connected with rotatable shaft 62 or the mount piece 27 and the stationary portion 49 with the gear base as described in more detail below. Slip ring assembly 50 includes brush-style rotational contacts 52, 54 and ring-shaped stationary contacts 56, 58. Rotatable shaft 62 is a hollow cylindrical shaft having a lumen 63 extending therethrough.

Transducer 28 is operatively connected to shaft 62 via the mounting piece 29 so that transducer 28 rotates in response to rotation of shaft 62. Mounting piece 29 is a structure that is configured to support transducer 28 while providing additional functions. Various embodiments of the mounting piece can allow rotational motion of the transducer around a rotation axis, define part of a wire guide channel, and/or include a cavity for housing a transducer element as well as providing other features or functions as described herein. As illustrated in FIG. 3, a bore 64 extends along or substantially parallel to the rotation axis through mounting piece 29 and provides attachment to shaft 62 as well as defining a portion of the channel 30 or the lumen, which, in the illustrated embodiment is configured to accept a wire guide 42. Other embodiments do not include a side passageway as described later. In some embodiments, bore 64 includes a side passageway 66 that extends through mounting piece 29, which, in some embodiments can be used for fluid injection. Another example of such mounting pieces is explained in U.S. Provisional Application No. 61/885,155 (filed Oct. 1, 2013 and entitled "Over-The-Wire Ultrasound System"), and in U.S. patent application Ser. No. 14/501,745 (filed Sep. 30, 2014 and entitled "Over-The-Wire Ultrasound System"), which are incorporated herein by reference in their entirety.

Stationary contacts 56, 58 are part of a stationary mount piece 70 of slip ring assembly 50. Stationary mount piece 70 has a contact end 72 opposite a cable end 74 and a length that spans between contact end 72 and cable end 74. Mounted to the stationary mount piece 70 are the slip ring assembly 50, a pin 75, and shaft 62 that gears 77 and 79, respectively, are mounted to. Stationary mount piece 70 includes a bore 78 that spans between a contact end 72 and a cable end 74, wherein the bore 78 is sized to receive the shaft 62. As such, shaft 62 passes through bore 78 from the contact end 72 to the cable end 74. Another important feature of the joint between the bore 78 in stationary mount piece 70 and shaft 62 is that this joint is a bearing surface in order to allow shaft 62 to rotate with minimal friction. The contact end 72 is circular and is positioned at the control side of mounting piece 29. Contact end 72 is oriented so that stationary contacts 56, 58 are positioned generally normal to the rotation axis. As illustrated in one embodiment in FIG. 4, the cable end 74 is circular and includes pin 75 that is positioned on a face of cable end 74. Pin 75 is sized to receive and retain a drive gear 77 that is connected to a torque cable 60. Pin 75 is located on the face of cable end 74 of the stationary mount piece 70 to enable coupling of the drive gear 77 to a ring gear 79 that is coupled with shaft 62 (see FIG. 1). The drive gear 77 and the ring gear 79 are configured to interact with one another and are external gears, i.e., having teeth that point away from their axes of rotation. Alternate embodiments can include different interactive gears that do not include teeth, such as belt driven gears or friction gears, to name a few. The face of cable end 74 also includes two contact pads 81 that are positioned opposite the pin 75. Contact pads 81 are used to solder or weld transducer electrical wires 160 thereto. In the illustrated embodiment, the pin 75, bore 78, and the contact pads 81 are generally positioned in a lineal fashion on the face of the cable end 74. As described in more detail below, the pin 75, bore 78, and the contact pads 81 are positioned to align with respective lumens 170, 172, and 174 in a pusher piece 176.

Stationary portion 49 of the stationary mount piece 70 includes stationary contacts 56, 58 in the illustrated embodiment (FIGS. 3 and 4) is constructed from printed circuit board methods of manufacture including photolithography and etching. In the illustrated embodiment, the stationary portion 49 is constructed as a flexible printed circuit board and is layered, having alternating conductive hard-gold plated nickel or copper and insulative polyimide layers. A topmost conductive layer 80 includes stationary contacts 56, 58. Wires (not illustrated) provide electrical connectivity between stationary contact 56 and contact pads 81 in cable end 74. Beneath layer 80 is an insulative layer 82, which electrically isolates stationary portion 49 from other components. The conductive layer 80 is electrically connected to contact pads 81 by a conductive path such as a wire or other means (not illustrated) through the stationary mount piece 70 and carries an electrical signal through the stationary mount piece 70 to contact pads 81. The transducer electrical wires 160 which include a coaxial cable or other suitable conductors (FIG. 1) are attached to both contact pads 81 in cable end 74 to carry signals to the control end of device 20.

Figure 5:
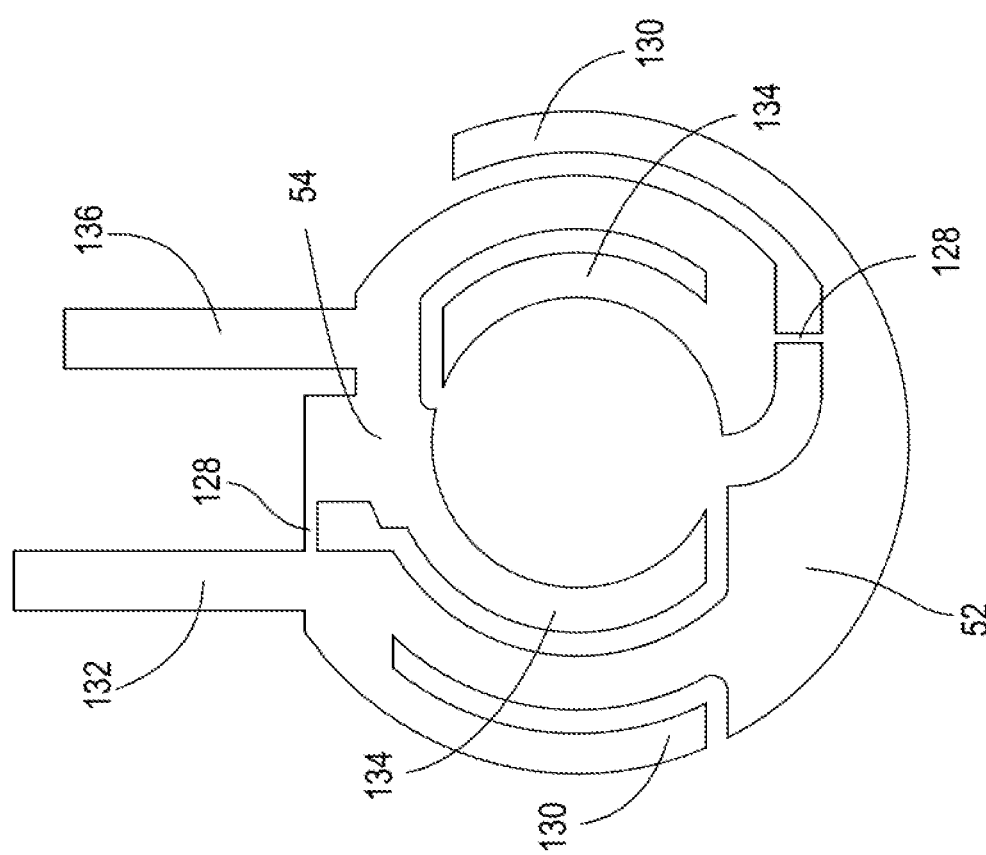
FIG. 5 is an illustrative front view of a rotational contact portion of the slip ring assembly of the FIG. 3 embodiment.

Rotational contacts 52, 54 are attached to mounting piece 29 in the illustrated embodiment. In the illustrated embodiment, rotational contacts 52, 54 are individual metal pieces that are stamped or otherwise manufactured from the same sheet of metal as illustrated in FIGS. 5 and 6. In the illustrated embodiment, rotational contacts 52, 54 are two separate electrical lines. Rotational contact 52 has two brush prongs 130 and a conductor prong 132. Similarly, rotational contact 54 has two brush prongs 134 and a conductor prong 136. Other embodiments include more or less brush prongs as appropriate.

In some embodiments, rotational contacts 52, 54 are a flexible printed circuit board. In some embodiments, rotational contacts 52, 54 are insert molded into mounting piece 29. In other embodiments, rotational contacts 52, 54 are integrated into mounting piece 29 using a hot embossing process or with a hot-staking process. In other embodiments, rotational contacts 52, 54 may be configured as conductive traces positioned on or into mounting piece 29 using electroless plating of metalizable plastic and/or a laser direct structuring technique.

Figure 8:
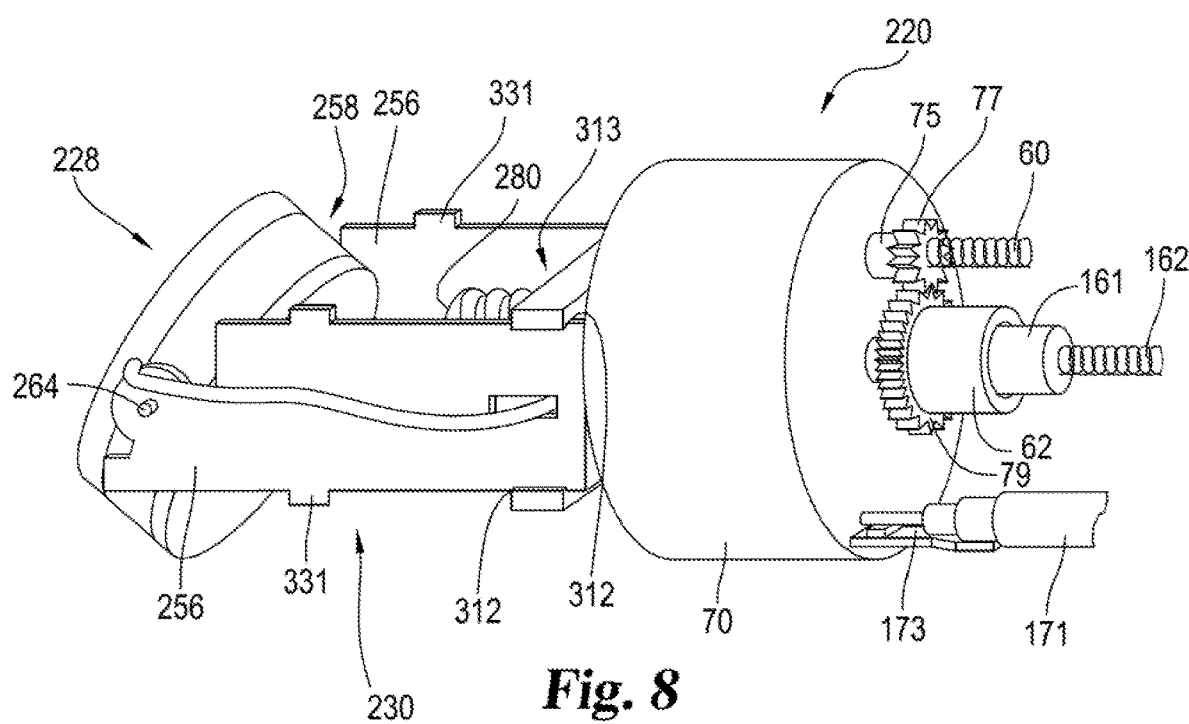
FIG. 8 is a perspective view of a portion of an embodiment of a three-dimensional ultrasound device in a first condition.
Figure 9:
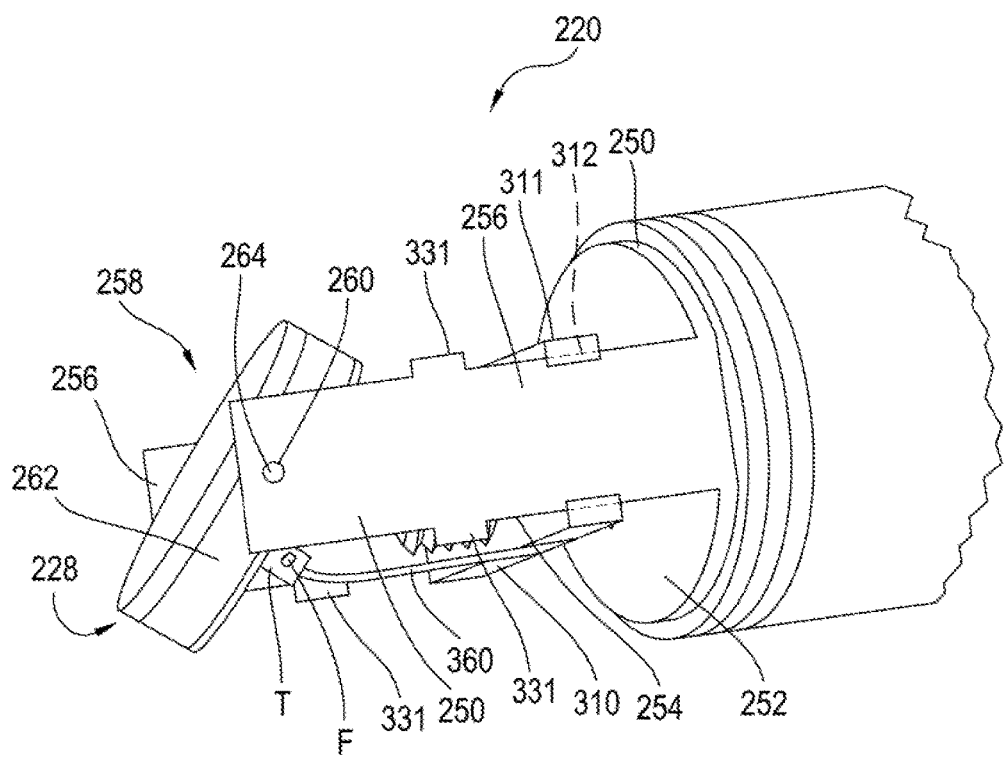
FIG. 9 is a perspective view of a portion of the device of FIG. 8 in a second condition.
Figure 10:
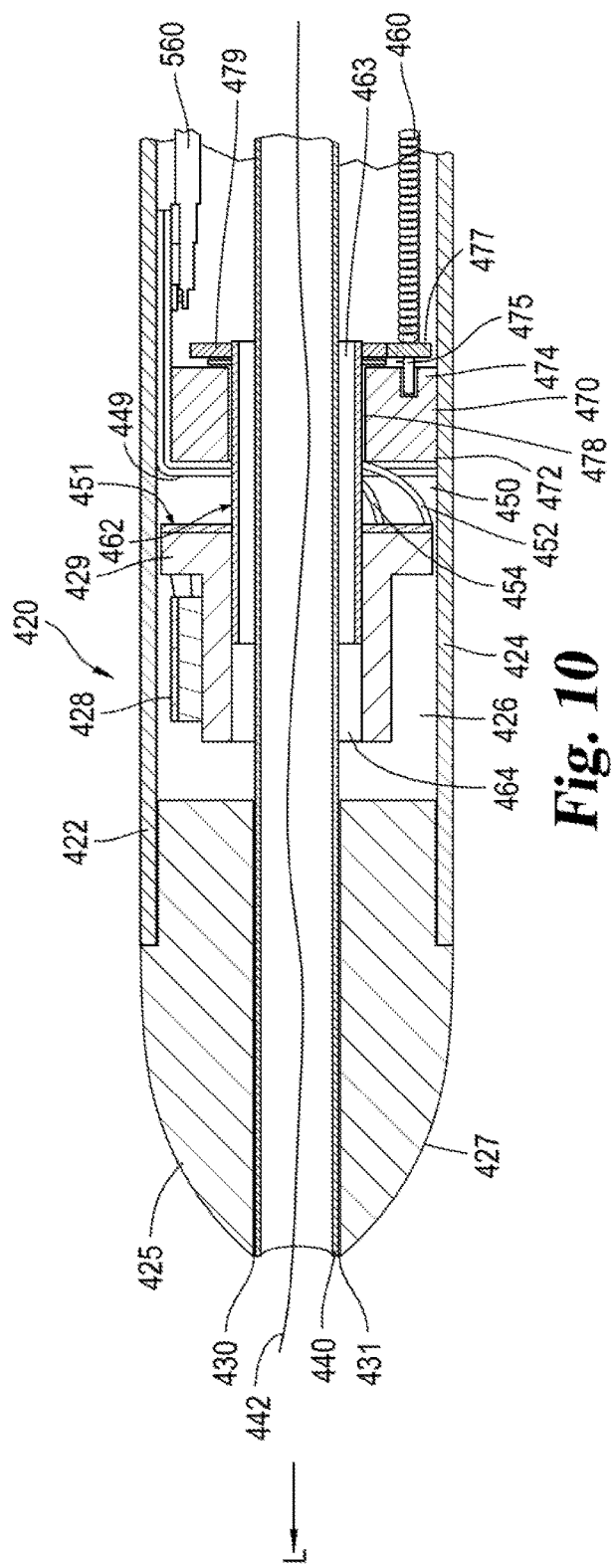
FIG. 10 is an illustrative cross-sectional view of a portion of an alternative embodiment of an ultrasound device having an isolated wire guide lumen.

The rotational contacts 52, 54 are designed to attach to transducer 28 or other rotating part of device 20 that is generally normal to the rotation axis (similar connection illustrated in FIGS. 8, 9, and 10). In some embodiments, the connections are made through mounting piece 29 using laser direct structuring process (LDS) and/or electroless plating of metalizable regions of the plastic.

During construction, in some embodiments, tabs 128 hold rotational contacts 52 and 54 relative to each other while the contacts are attached to mounting piece 29 using glue, fasteners, or another suitable attachment method. After rotational contacts 52 and 54 are attached to mounting piece 29, tabs 128 are cut and removed so that rotational contact 52 is physically and electrically separated from rotational contact 54. Mounting piece 29 is constructed from (or coated wholly or partially with) an electrically insulative material so that it acts as an insulator between rotational contacts 52 and 54.

Conductor prongs 132, 136 are bent around mounting piece 29 and attached to transducer 28 to form the signal and ground channels, which are then connected to transducer 28. Brush prongs 130 are positioned to abut against and slide along stationary contact 56, and brush prongs 134 are positioned to abut against and slide along stationary contact 58. Brush prongs 130, 134 are bent to an angle to create a spring force when brush prongs 130, 134 are positioned to abut against stationary contacts 56, 58. Contact end 72 of stationary mount piece 70 is positioned generally normal to the rotation axis and parallel to the control side surface of mounting piece 29 that supports rotational contacts 52, 54. This arrangement coupled with the spring force in the bent portions of brush prongs 130, 134 help to ensure a stable connection. Rotational contacts 52, 54 include multiple brush prongs which also help to ensure stable connection. In other embodiments (not shown), rather than using spring contacts, an elastically compressible polymer is used for the brush portion which is an elevated portion of mounting piece 29 with conductive traces printed/plated on top of the elevated regions that are configured to contact stationary contacts 56, 58.

It should be noted that for the sake of clarity, device 20 in FIGS. 1, 2, and 3 is depicted with mounting piece 29 positioned slightly away from stationary mount piece 70 so that rotational contacts 52, 54 are not in contact with stationary contacts 56, 58. For proper functioning, mounting piece 29 is positioned close enough to stationary mount piece 70 to make functional electrical connections between the stationary contacts and rotational contacts such as in an assembled configuration.

In some embodiments, either or both of rotational contacts 52, 54 and/or stationary mount piece 70 has a finish layer that includes a layer or layers of beryllium copper, nickel, tin, gold, palladium, silver, hard gold (e.g. AuCo, AuNi, AuCoNi, etc.) or other noble metals and their alloys. The finish layer is designed to prevent corrosion in air or fluid as well as to not create debris within chamber 26 during use. In other embodiments of pancake-style slip rings (not shown), the stationary contacts can include brush prongs and the rotational contacts can include planar surfaces configured to abut against the brush prongs. Other examples of slip ring designs are explained in International Application No. PCT/US2013/064611, filed on Oct. 11, 2013, published as WO 2014/059292 A1, and entitled "INTERNAL TRANSDUCER ASSEMBLY WITH SLIP RING", which is hereby incorporated by reference in its entirety.

Figure 7:
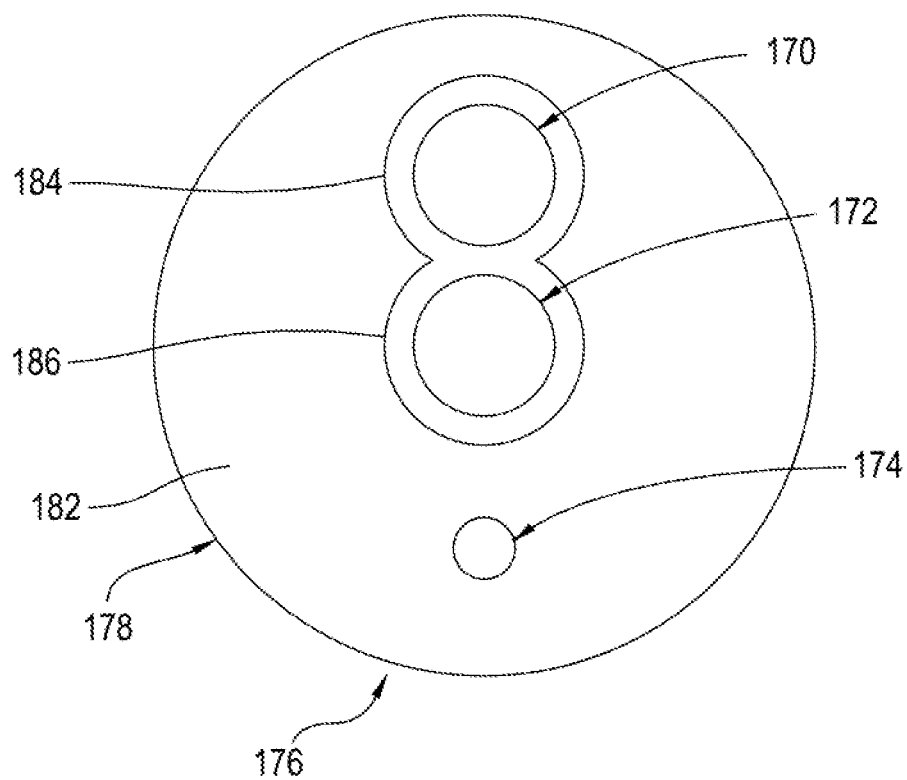
FIG. 7 is an illustrative end view of one embodiment of a pusher piece from the device of FIG. 1.

As mentioned previously and illustrated in FIGS. 1, 2, and 7, pusher piece 176 includes lumens 170, 172, and 174 that span between an application end 178 and a control end 180. The application end 178 includes a face 182 with a first recess 184 that extends substantially around the lumen 170 and a portion of lumen 172. The first recess 184 is sized to receive the drive gear 77. The face 182 also includes a second recess 186 that extends substantially around the lumen 172 and a portion of lumen 170. The second recess 186 is sized to receive the ring gear 79. As such, the first recess 184 and the second recess 186 are arranged and sized to collectively receive the drive gear 77 and the ring gear 79, respectively. In an assembled configuration, the pusher piece 176 is butted up to the stationary mount piece 70 such that the drive gear 77 nests with the first recess 184 and the ring gear 79 nests with the second recess 186.

Lumen 170 is sized to receive the torque cable 60. In one embodiment, lumen 170 is reinforced to avoid abrasion of the torque cable 60 when the device 20 is being used. Lumen 172 is sized substantially the same as the bore 78 to enable the wire guide 42 and fluid to pass through lumen 172 and into bore 78 for a fluid passageway. As such, fluid flushes into the mounting piece 29 and out the side passageway 66 to fill chamber 26. In an alternative embodiment, lumen 172 is sized to fit a metal or polymer tubing that seals between the wire guide 42 and the chamber 26. In this embodiment, lumen 172 is sealed on the tip side and on the side of the stationary mount piece that is closer to the control end to contain the coupling fluid within chamber 26. Lumen 174 is sized to receive the transducer electrical wires 160 and the contact pads 81. In one form, pusher piece 176 is made of a flexible plastic rod. As described in more detail below, the pin 75, bore 78, and the contact pads 81 are positioned to align with respective lumens 170, 172, and 174 in a pusher piece 176. Lumens 170, 172, and 174 maintain the torque cable 60, wire guide 42, and transducer electrical wires 160, respectively, from becoming entangled with one another after assembly of the device 20.

Motor 100 is mechanically connected with the torque cable 60 to operatively drive the gear 77 which drives the gear 79 that is connected to the shaft 62. Shaft 62 in turn drives the mounting piece 29 and the transducer 28. As illustrated the motor 100 is placed remotely and will drive the mounting piece 29 and the transducer 28 via the long torque cable 60. Beneficially, the motor 100 is not placed within the catheter 22 but is positioned outside and a distance from the catheter 22 therefore the size of motor 100 may vary as desired. The motor 100 is external to the catheter 22 and could be mounted on the handle or connected to the handle to transfer torque to the torque cable 60. It could be any type of motor, electrically driven, pneumatically, or hydraulically driven. It could also be driven by the operator via a crank handle.

In operation, motor 100 turns the torque cable 60 about its longitudinal axis, which in turn drives or rotates the drive gear 77. The drive gear 77 is coupled to the ring gear 79 such that rotation of the drive gear 77 rotates ring gear 79 which in turn rotates mounting piece 29 that is connected to the ring gear 79 via the shaft 62. Thus rotating the torque cable 60 in turn rotates the mounting piece 29 and the transducer 28, albeit in the opposite direction.

Motor 100 may be configured to rotate torque cable 60 and thus mounting piece 29 continuously in a single rotational direction. In such embodiments, transducer 28 is rotated around the rotation axis in that single rotational direction. Appropriate feedback mechanisms may be used to precisely control the rotational position of mounting piece 29 (and transducer 28 rotated by it) relative to the rest of device 20, ensuring proper registration of images obtained through transducer 28. Registration can be accomplished via methods and structures discussed in U.S. Provisional Application No. 61/713,142 (filed Oct. 12, 2012 and entitled "Feedback/Registration Mechanism for Ultrasound Devices") which is incorporated by reference herein in its entirety. Motor 100 may alternatively be configured to run in a reciprocating motion, with torque cable 60 switching between rotation in a first rotary direction (e.g. for a predetermined time, arc or number of turns) and rotation in a second, opposite, rotary direction (e.g. for a predetermined time, arc or number of turns). Methods and structures relating to a reciprocating motor are discussed in U.S. Provisional Application No. 61/713,135 (filed Oct. 12, 2012 and entitled "Reciprocating Internal Ultrasound Transducer Assembly") which is incorporated by reference herein in its entirety.

An example of using device 20 will now be given. This embodiment of device 20 is typically charged or injected with coupling medium prior to insertion into the patient's body, e.g. before a wire guide or other tool or structure is placed in channel 30. In one form, chamber 26 is pre-filled with coupling medium during production. Thereafter, device 20 is inserted into the body of a patient, and/or maneuvered to a desired location (e.g. in a particular blood vessel). In alternative embodiments, however, the device 20 may be charged (or further filled or refilled) with coupling medium following insertion into the patient's body, or may occur during insertion and transducer 28 may be operated during travel to the desired location. It will be understood that filling or refilling can be done with structure (e.g. wire guide 42) inside channel 30, or with channel 30 otherwise empty. Additionally, particular embodiments of catheter 22 or at least chamber 26 are cylindrical, and are sized for insertion into and passage through body conduits.

Appropriate coupling medium is selected, such as saline, oils, alcohols or other appropriate ultrasound-transmissive fluids, so as to give chamber 26 ultrasound characteristics similar or substantially identical to that of wall 24 and the surrounding bodily environment (e.g. the blood stream). The coupling medium is loaded into a syringe with a needle (not shown) or other appropriate injection, insertion or transfer device. Coupling medium may be injected into channel 30 at or near the control end of the catheter 22, or otherwise at an entry location into channel 30, so as to urge the coupling medium to travel within channel 30 toward chamber 26. In certain embodiments, the coupling medium may be forced through the needle and into channel 30 via pressing a syringe plunger. Prior to, during and/or following injection of the coupling medium, motor 100 is activated to cause mounting piece 29 to rotate about the rotation axis R. Upon reaching mounting piece 29, the coupling medium is urged into the passageway 66 and out into chamber 26 by centrifugal action or inertial force as a result of rotation of mounting piece 29 about the rotation axis R.

As the coupling medium enters the chamber 26, it displaces the gas within chamber 26 by increasing the pressure on such gas (e.g. air). The increased pressure forces the gas out of chamber 26 through open end 38 to the external area outside of device 20. Injection of coupling medium continues until chamber 26 is filled to a satisfactory degree, for example when a predetermined amount of medium has been injected, and/or a maximum amount of the gas previously in chamber 26 has been replaced with coupling medium. As a result, the chamber 26 is filled with coupling medium to an extent that there are no visible gas pockets or bubbles present around transducer 28, as gas pockets or bubbles have an acoustic impedance significantly different from the coupling medium, and thus can reflect or otherwise attenuate ultrasound waves.

The charging and exhaust effects occurring with respect to the illustrated device do not require space within the wall 24 of catheter 22, as is needed for the placement of other types of tubes or ports required for charging. Such space considerations can be quite important for uses of ultrasound in small areas, such as cardiovascular (e.g. peripheral vascular) applications. As will be appreciated, the illustrated arrangement also provides the ability to flush the catheter with and/or add coupling medium from an access at or near the control end and while the catheter is in situ, if deemed necessary by the medical professional.

Motor 100 may be operated to turn transducer 28 around the rotation axis R to provide the desired imaging at one or more different times throughout the procedure. As examples, the transducer 28 may be rotated during injection of the coupling medium, during travel and placement of the catheter, and/or at the final desired imaging location. The option of providing imaging while coupling medium is injected into the device and enters the chamber 26 allows the user to evaluate the fill status of the chamber 26 and determine when complete fluid coupling occurs. In such embodiments, the user console may be configured to provide notifications to the user indicating the fill status of the chamber 26 and/or indicating the presence of gas pockets or bubbles, or providing indications of other issues pertaining to the user of the device.

At a desired imaging location (and optionally throughout fluid fill and catheter placement), motor 100 can be operated to turn transducer 28 around the rotation axis R to provide images of tissue(s) or other matter around device 20, and in certain optional embodiments to pivot the transducer about a pivot axis. When an ultrasound signal is transmitted, the ultrasound signal passes through wall 24 of catheter 22 until it encounters an acoustic impedance boundary (e.g. body tissue, plaque, medical implant, or other material which has acoustic impedance sufficiently different from bodily fluids or other surrounding material) such that the ultrasound signal is at least partially reflected at the boundary. At least a portion of the ultrasound signal is reflected back towards transducer 28. One or more electrical signals representing reflected ultrasound received at transducer 28 are sent from transducer 28 via a conduction pathway to the ultrasound console, for imaging and/or other data display to the physician. Simultaneously or subsequently transducer 28 continues to emit further ultrasound signals and the process is repeated continuously in certain embodiments and over a desired period of time. Controls for motor 100 may be provided to maintain rotational motion of transducer 28 about the rotation axis at a particular rotational speed or pattern. Imaging continues, with adjustments to the positioning of transducer 28 and the ultrasound field, as the physician deems necessary or useful. Once the desired therapeutic, diagnostic, imaging or other ultrasound procedure is performed, the device can be removed.

Catheter 22 has at least a portion that presents a minimal barrier to the passage of ultrasound signals so that ultrasound images of surrounding matter (e.g. tissue(s) or implant(s)) may be reasonably acquired through the barrier. For example, catheter 22 may have at least a portion that is constructed of a material which is substantially echolucent (i.e. having small ultrasound attenuation, having similar acoustic impedance or small difference in acoustic impedance with the surrounding environment) when placed in the surrounding working environment, such that it acts as an acoustic window which allows passage of ultrasound signals with minimal reflection. It will be understood that only the application end of catheter 22 (e.g. wall 24) need be acoustically transparent, but more or all of catheter 22 and/or other components thereof may be made of the same material in some embodiments. For example, when used within a body conduit containing body tissues and blood, it is preferable for catheter 22 to be constructed of a material which is structurally rigid and which has acoustic impedance similar to that of body fluids such as blood. Possible materials could include, for example, a polymer material such as high density polyethelene, polymethylpentene (PMP), or acrylonitrile butadiene styrene (ABS). It has been determined that in some cases the thickness of at least the portion of catheter 22 which serves as the viewing window can be approximately N/2 (where N is a positive integer) of the wavelength corresponding to the center frequency of the ultrasound signal.

Although particular materials were highlighted herein for some components of device 20, those materials are not intended to be limiting of the types of materials which are suitable to be used in device 20. Additionally, where materials were not highlighted, a variety of materials could be used such as certain types of metals, polymers, ceramics or other types of materials which are suitable for use in devices for small body cavity applications.

Device 20 could also be used for a variety of other medical procedures and with a variety of other medical devices. Accordingly, the particular methods of use described herein are not indicative of any limiting aspects of the usage capabilities of device 20.

FIGS. 8 and 9 represent an alternate embodiment of structure of a device 220 for internal ultrasound procedures. This embodiment of device 220 includes a transducer 228, pivoting mechanism 230, a first torque cable 60, a second torque cable 162, a coaxial cable 171, and one or more slip disk connection pads 173. The features of device 220 are intended in particular embodiments to be housed within a catheter, essentially as described above with respect to device 20 and catheter 22.

Torque cable 60 connects to drive gear 77 which is mounted on pin 75, similarly as described above. Ring gear 79 is coupled with shaft 62 wherein drive gear 77 and ring gear 79 are configured and positioned to interact with one another as described above. Torque cable 60 is connected to drive gear 77 wherein the torque cable 60 causes the drive gear 77 to rotate to thereby rotate the ring gear 79 to rotate the shaft 62 and the transducer 228. A through shaft 161 passes through shaft 62 and stationary mount piece 70 to a threaded shaft 280. There is some clearance between through shaft 161 and shaft 62 so that shaft 62 can rotate without coming in contact with through shaft 161. In an alternate embodiment, through shaft 161 and threaded shaft 280 are a single component.

Shaft 280 passes through hollow shaft 62 with a portion of the distal end of shaft 280 extending beyond the end of shaft 62. In the illustrated embodiment, shaft 280 is threaded over its entire length, while in other embodiments shaft 280 may be threaded only over one or more discrete portions, e.g. a portion that passes through hollow shaft 62 and extends beyond hollow shaft 62. For example, in an alternative embodiment, wherein through shaft 161 and threaded shaft 280 are a single component, shaft 280 may be threaded only over one or more discrete portions. Shaft 280 is able to turn within and independently of shaft 62. The rate of rotation of torque cable 162 controls the rate of rotation of threaded shaft 280. As will be discussed further below, the relative rates of cables 60 and 162 provide pivoting action for transducer 228. Transducer 228 is similar to transducer 28. Transducer 228 is mounted in pivoting mechanism 230 to permit transducer 228 to turn around a rotating axis as well as pivot around a pivoting axis. The illustrated embodiment of mechanism 230 is a gimbal-type mounting, having an outer frame piece or base 250 including a center portion 252 with a hole 254 therethrough and matching arms 256 extending laterally of hole 254 from center portion 252. Center portion 252 is fixed to or with respect to shaft 62 so that shaft 62 can turn pivoting mechanism 230. Hole 254 is sized and configured to threadedly accommodate a portion of shaft 280. A pivoting element 258 fits into holes 260 in arms 256 in the embodiment of FIGS. 8 and 9. Pivoting element 258 in the illustrated embodiment is a circular disk 262 having side ears or pivot points 264 that fit into holes 260 and act as an axle, so that element 258 can pivot around the axis defined by ears 264. In particular embodiments, pivoting element 258 may be a backing, base or substrate on which all or a part of transducer 228 is fixed, or may be a portion of transducer 228.

Mechanism 230 in this embodiment includes a sliding member or plate 310 in contact with arms 256. Plate 310 has respective lateral sides 311 in this embodiment each having top and bottom grooves 312. Arms 256 of mechanism 230 are within grooves 312 of sliding member or plate 310, so that plate 310 can slide along the arms, moving linearly with respect to mechanism 230. Plate 310 includes an opening 313 therethrough, which in the illustrated embodiment is substantially in the center of Plate 310. Plate 310 may be thin so that the rim or edge of opening 313 acts as a thread that is compatible with the thread of shaft 280, or the rim or edge of opening 313 may be internally threaded so as to engage the threads of threaded shaft 280.

In the illustrated embodiment, the range of movement of plate 310 along arms 256 is defined by limit stops 331 on the arms of the pivoting mechanism 230. Limit stops 331 are shown in this embodiment as raised portions or bosses extending from the arms, e.g. a square or rectangular tab in the plane of and monolithic with the arm 256. The sites of limit stops 331 determine the maximum amount of movement of plate 310 by creating a location relative to arms 256 at which plate 310 is blocked from further sliding along arms 256. In particular embodiments, limit stops 331 are placed only at a location distal of center portion 252, so that plate 310 can slide at most between center portion 252 (acting as a control-side limit stop) and limit stops 331, while in other embodiments a set of limit stops 331 may be placed inside center portion 252 and another set of limit stops 331 further distally. Part or all of plate 310 and/or of arms 256 can be made from or coated with a low friction material (e.g. PTFE (Teflon)) to make the sliding of plate 310 over arms 256 easier.

Because plate 310 is connected to arms 256, it rotates along with pivoting mechanism 230 at a rate of speed that is determined by the rotation of shaft 62 by torque cable 162. Plate 310 is also threadedly connected to shaft 280, as threads of shaft 280 engage plate 310 through opening 313. The rate of rotation of threaded shaft 280 is determined by torque cable 162.

When the rates of rotation of shafts 62 and 280 are the same, i.e. the relative rotational speed of the shafts is zero, then there is no relative rotation between plate 310 and shaft 280, and so threaded shaft 280 does not force plate 310 in either direction along arms 256. When there is a non-zero relative rotational speed between shafts 62 and 280, then there is a relative rotation between shaft 280 and plate 310, and the threaded engagement between shaft 280 and plate 310 results in longitudinal movement of plate 310 along shaft 280 and arms 256.

A forcing member 360 is attached to plate 310, and in the illustrated embodiment member 360 is connected to pivoting element 258 on one end and to the side of the pivoting axis. As an example, pivoting element 258 can include a tab T that extends from pivoting element 258 opposite (e.g. substantially perpendicular) from transducer 228. Forcing member 360 can include a distal finger F that connects to tab T, as by extending through a hole or slot in tab T (e.g. FIGS. 8 and 9), so that member 360 can pivot with respect to tab T. With forcing member 360 attached to plate 310 and connected to pivoting element 258, movement of plate 310 causes the forcing member 360 to apply force to pivoting element 258, which rotates pivoting element 258 (with transducer 228) around the axis defined by ears 264.

Forcing member 360 in the illustrated embodiment is a flattened bar that preferably has little or no longitudinal elasticity, so that movement of plate 310 is efficiently transmitted to pivoting element 258. A suitable forcing member may be of other shapes or materials that provide for transmission of enough force to pivot element 258 when sliding plate 310 moves along arms 256, such as a C-shaped wire structure or similar member described above. Mechanism 230 permits transducer 228 to turn around a rotating (e.g. longitudinal) axis, via transmission of rotational motion from torque cable 60 to mechanism 230 via shaft 62.

Mechanism 230 permits pivoting of transducer 228 around a pivoting axis (e.g. perpendicular to the rotating axis) at the same time, via pulling or pushing force on pivoting element 258 transmitted via member 360 from sliding plate 310. Plate 310 is moved along arms 256 when the rotational speed of threaded shaft 280 is different from the rotational speed of shaft 62, so that a nonzero rotational speed of shaft 280 relative to shaft 62 exists. In the latter case, the threaded engagement of shaft 280 and plate 310 causes plate 310 to slide along arms 256. Pivoting element 258 is thus able to rotate about both the pivoting and axial directions.

It will be understood that changing or fluctuating of the rotational speed of one or both of shafts 62 and 280 can generate a reciprocating pivoting movement of pivoting element 258. For example, if the rotational speed of shaft 62 is held steady at a value V, and the rotational speed of shaft 280 fluctuates uniformly, steadily or step-wise from a value V+v to a value V-v, then the effect is a reciprocating pivoting motion. There is no pivoting when both rotational speeds are V, and that condition can correspond to pivoting element 258 and plate 310 being at extreme positions (e.g., with plate 310 abutting or close to a limit stop 331 or base 250 of mechanism 230). When the speed of shaft 280 is greater than V (i.e. between V and V+v or at V+v), then plate 310 moves in a one linear direction along arms 256 (either toward or away from base 250), and pivots element 258 in one angular direction (either clockwise or counterclockwise). When the speed of shaft 280 is less than V (i.e. between V and V-v or at V-v), then plate 310 moves in the other linear direction along arms 256, and pivots element 258 in the other angular direction.

With mechanism 230, it is possible to arrange pivoting of pivoting element 258 from a first position that is substantially forward-looking (e.g. FIG. 8), so that transducer 228 points along or substantially along a longitudinal axis of device 220, to a second position that is somewhat rearward-looking, so that transducer 228 points in a direction more than 90 degrees behind that forward-looking first position (i.e., past perpendicular to the longitudinal axis). Device 220 thus has the ability to look forward using ultrasound, as well as having a very wide angle and volume of available viewing through ultrasound transmission. Further details regarding the motion mechanism are described in International Application No. PCT/US2013/064570 filed on Oct. 11, 2013 and published as WO 2014/059292, which is incorporated by reference.

FIG. 10 represents an alternate embodiment of a device 420 for internal ultrasound procedures. This embodiment of device 420 includes similar features as device 20. Device 420 includes a catheter 422 similar to catheter 22 having a wall 424 and extending along a longitudinal axis L and a catheter tip 425 having a wall 427 and extending along the longitudinal axis L. Wall 424 has an inner surface defining an internal chamber 426, within which is included a mounting piece 429 housing a transducer 428. Wall 424 surrounds chamber 426 which is near the application end of the device 420. The application end of wall 424 is sized and configured to receive and retain catheter tip 425.

In this embodiment, chamber 426 is pre-filled with a coupling medium during manufacture of device 420. Cannula 440 extends a partial or full length of channel 430. Cannula 440 contains the wire guide lumen, and allows for the wire guide lumen to be isolated from chamber 426, which allows for chamber 426 to be pre-filled with coupling medium during manufacturing of device 420.

Transducer 428 is similar to transducer 28 therefore for the sake of brevity will not be described again. Transducer 428 is operably linked to a motor (positioned exterior to the catheter 422) via a torque cable 460 to permit transducer 428 to turn, pivot, or otherwise move.

A channel 430 extends from the control end to the application end of the catheter 422. Channel 430 includes a tubular opening 431 sized to receive a cannula 440 sized and configured to receive a wire guide 442. The cannula 440 is configured to seal the chamber 426 to block any fluid in the chamber 426 from entering or contacting the wire guide 442 inside cannula 440. Although not illustrated, a seal is formed near a stationary mount piece 470 and with the cannula 440. The chamber 426 is completely sealed off from the rest of the catheter 422 and can be pre-filled during production with oil or other non-corrosive and biocompatible coupling mediums and then the chamber 426 is sealed closed. As such, mounting piece 429 does not include a passageway to chamber 426 for filling the chamber 426 as in FIGS. 1 and 2.

Cannula 440 is an elongated structure such as a metal tube or polymer or plastic tubing having a lumen to receive the wire guide 442 wherein the cannula 440 passes through catheter tip 425, mounting piece 429, a hollow shaft 462, and a slip ring assembly 450. Cannula 440 can be configured to accept varied sizes of wire guides and align with channel 430. In the illustrated embodiment, cannula 440 is positioned in channel 430.

Device 420 includes a slip ring assembly 450 and a hollow shaft 462 similar to slip ring assembly 50 and hollow rotatable shaft 62, respectively, discussed above. Slip ring assembly 450 includes a stationary portion 449 and a rotating portion 451. A motor (not illustrated) positioned exteriorly to the wall 424 is operatively connected with rotatable shaft 462 or the mounting piece 429 while the rotating portion 451 of the slip ring assembly 450 is operatively connected with the mounting piece 429 and the stationary portion 449 with the gear base. Slip ring assembly 450 includes brush-style rotational contacts and ring-shaped contacts as described above. Rotatable shaft 462 is a hollow cylindrical shaft having a lumen 463 extending therethrough.

Transducer 428 is operatively connected to shaft 462 via the mounting piece 429 so that transducer 428 rotates in response to rotation of the shaft 462. A bore 464 similar to bore 64 extends along or substantially parallel to the rotation axis through mounting piece 429 and provides attachment to the shaft 462. Bore 464 is also sized to receive cannula 440 therein; however, cannula 440 does not rotate.

A stationary mount piece 470 is similar to stationary mount piece 70 described above and includes a contact end 472 opposite a cable end 474 and a length that spans between contact end 472 and cable end 474. Mounted to the stationary mount piece 470 are the slip ring assembly 450, a pin 475, and shaft 462 that gears 477 and 479, respectively, are mounted to. Stationary mount piece 470 includes a bore 478 that spans between contact and cable ends and is sized to receive the shaft 462 wherein the shaft 462 passes through bore 478. Another important feature of the joint between the bore 478 in stationary mount piece 470 and shaft 462 is that this joint is a bearing surface in order to allow shaft 462 to rotate with minimal friction. The cable end 474 includes a pin 475 similar to pin 75. Pin 475 is sized to receive and retain a drive gear 477 that is connected to a torque cable 460. Pin 475 is located on the face of the cable end 474 to enable coupling of the drive gear 477 to a ring gear 479 that is coupled with shaft 462. Similar to gears 77 and 79, the drive gear 477 and the ring gear 479 are configured to interact with one another and are external gears. In this embodiment, a coaxial cable 560 or other suitable conductor is electrically connected with stationary portion 449 to carry signals to the control end of the device 420.

Stationary portion 449 of the stationary mount piece 470 is similar to the stationary portion 49 described above. Rotational contacts 452, 454 are similar to rotational contacts 52, 54 and are attached to the mounting piece 429. Therefore similar features for stationary portion 449 and stationary mount piece 470 will not be described again. It should be noted that for the sake of clarity, device 420 in FIG. 10 is depicted with mounting piece 429 positioned slightly away from stationary mount piece 470. For proper functioning, mounting piece 429 is positioned close enough to stationary mount piece 470 to make functional electrical connections between the stationary contacts and rotational contacts such as in an assembled configuration.

A pusher piece similar to pusher piece 176 described above may be used with catheter 422; however, the pusher piece not shown in this embodiment.

A motor (not illustrated) is connected with torque cable 460 to operatively drive gear 477 which drives gear 479 that is connected to the shaft 462. Shaft 462 in turn drives the mounting piece 429 and the transducer 428. The motor is placed remotely and is positioned outside catheter 422. The motor for embodiment illustrated in FIG. 10, is similar to motor 100 discussed above. As gear 477 rotates, gear 477 causes gear 479 to also rotate to thereby transfer rotation from a central axis in gear 477 to a central axis in gear 479, in other words, from an axis off center of the rotation axis of the transducer 428 to the central axis or channel 430 of the catheter 422.

An example of filling a catheter tip 425 prior to use is described next. At least one syringe (most likely two) would need to be used to do this injection through the tip wall 427. As the syringe is pulled out, the material around the needle self-seals, keeping the coupling medium from escaping from a chamber 426. This filling method also requires that the wire guide lumen be sealed off or isolated from the chamber 426 or that there be no wire guide lumen.

Alternatively, during a production step in which the catheter is not fully assembled and during the assembly process the chamber 426 is filled with coupling medium and then sealed such that the coupling medium does not leak out of it.

Figure 11:
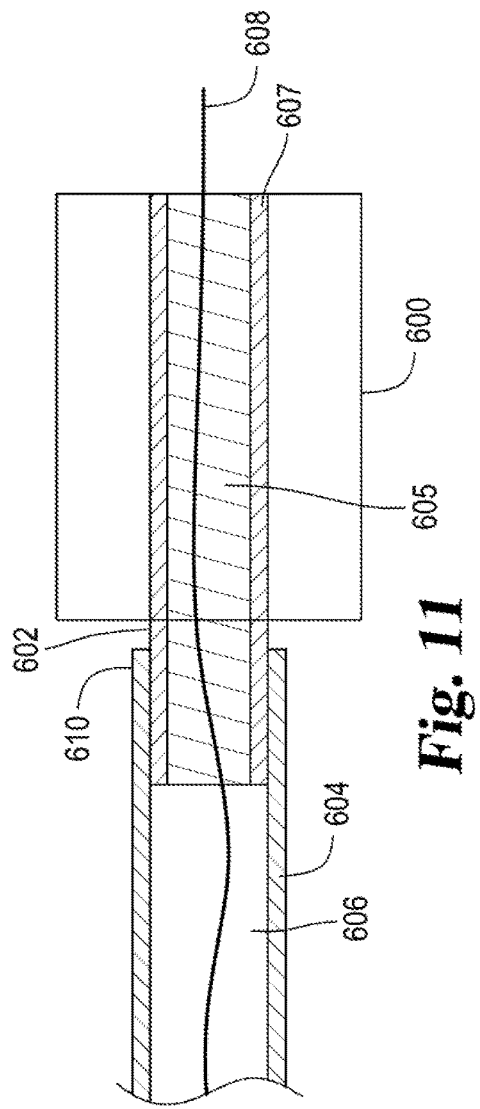
FIG. 11 is an illustrative cross-sectional view of a portion of an alternative embodiment of an external motor having a hollow shaft and a hollow torque cable attached to the hollow shaft for use with an ultrasound device.

FIG. 11 represents an alternate embodiment of an external motor 600 with a hollow shaft 602 operably attached to the motor 600 for use with a hollow torque cable and an over the wire catheter as described above and in FIG. 13. The motor 600 includes the hollow shaft 602. Other embodiments may not include the hollow shaft 602 but instead include an alternative connection between the motor 600 and the hollow torque cable 604. The hollow shaft 602 defines a lumen 605 that is sized to receive a wire guide 608 therein and a wall 607 that surrounds the lumen 605 wherein the wall 607 has a thickness and a length that is sufficient to receive and retain a distal end of the hollow torque cable 604 thereon. The hollow shaft 602 is operably connected to a hollow torque cable 604 such that the torque cable 604 is driven directly by the hollow shaft 602 and the motor 600. The hollow torque cable 604 includes a lumen 606 sized and configured to receive the wire guide 608 therein. As such the wire guide 608 passes through the lumen 605 of the hollow shaft 602 and the lumen 606 of the hollow torque cable 604. The hollow torque cable 604 includes a distal end 610 opposite a proximal end (not illustrated) wherein the proximal end is operably connected to a hollow shaft 862 illustrated in FIG. 13 and described more below. When the hollow torque cable 604 is connected to the hollow shaft 862, the torque cable 604 and the hollow shaft 602 are aligned with the longitudinal axis of the housing. Moreover, a gear mechanism is not required in this embodiment illustrated in FIG. 11.

Figure 12:
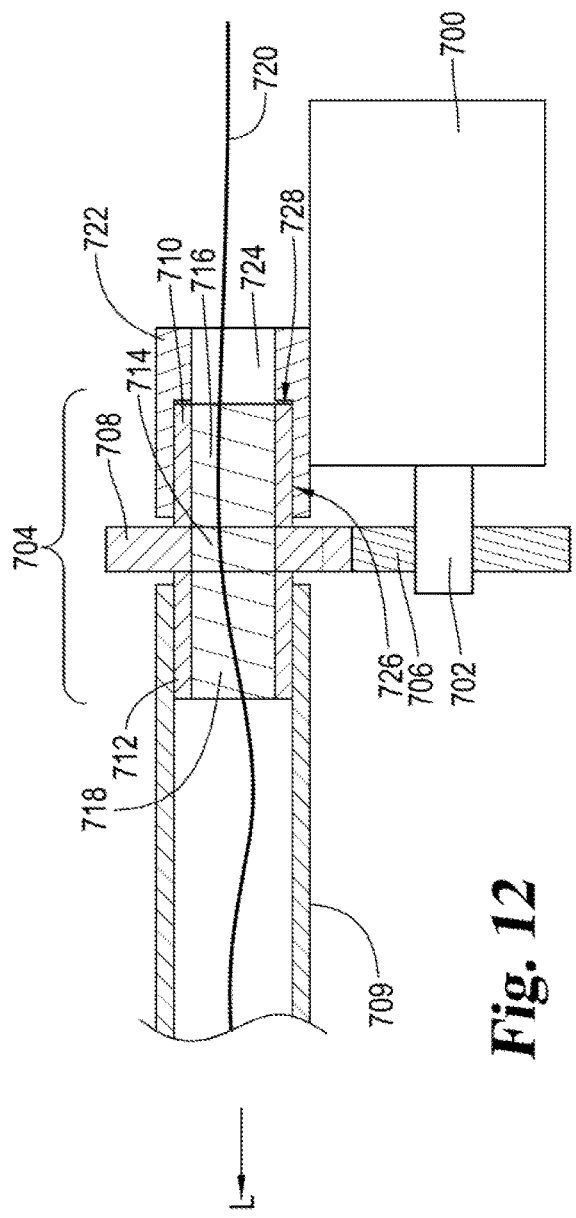
FIG. 12 is an illustrative cross-sectional view of a portion of an alternative embodiment of an external motor having a gear assembly attached thereof and a hollow torque cable for use with an ultrasound device.

FIG. 12 represents an alternate embodiment of an external motor 700 with a solid shaft 702 operably attached to the motor 700 for use with an over the wire catheter as described above and in FIG. 13. The solid shaft 702 has a cylindrical shape and a solid cross-section. In alternate embodiments, the shaft 702 includes an alternative configuration that may be hollow. Mounted onto the shaft 702 is a gear assembly 704 that includes a first gear 706 rotatably mounted onto the shaft 702 and a second gear 708 operably connected to the first gear 706 as described below.

The gear assembly 704 includes a first peg 710 mounted on a first face of the second gear 708 and a second peg 712 mounted on a second face of the second gear 708. The first peg 710 or the second peg 712 enables a first connection between the second gear 708 and a stationary piece 722 and a second connection between the second gear 708 and a hollow torque cable 709. In an alternate embodiment, the first peg 710 and the second peg 712 can include a pin, a dowel, or some other type of connector element. The first gear 706 and the second gear 708 are configured and arranged to have an interactive relationship wherein the first gear 706 drives or moves the second gear 708 when the motor 700 is activated. The first gear 706 and the second gear 708 are configured to interact with one another and are external gears, i.e., having teeth that point away from their axes of rotation. Alternate embodiments can include different interactive gears that do not include teeth, such as belt driven gears or friction gears, to name a few. The first gear 706 is positioned adjacent to or offset a distance from a longitudinal axis L such that the first gear 706 has a rotational axis offset from the longitudinal axis L and the first gear 706 is rotatable about the rotational axis. The second gear 708 is positioned along the longitudinal axis L of the housing and the second gear 708 is configured to interact with the first gear 706 wherein the second gear 708, including the first peg 710 and the second peg 712, is rotatable about the longitudinal axis L when the first gear 706 rotates about the rotational axis. The second gear 708 defines a lumen 714 that is aligned with a lumen 716 on the first peg 710 and a lumen 718 on the second peg 712. The lumens 714, 716, and 718 are configured and aligned to receive a wire guide 720 therein. The first peg 710 and the second peg 712 each have a cylindrical shape. In the illustrated embodiment, the first peg 710 has the same length and cross-sectional shape and size as the second peg 712. In alternate embodiments, the first peg 710 can have a different length or cross-sectional shape than the second peg 712. Alternatively, the first peg 710 and/or the second peg 712 can be monolithic with the second gear 708.

The motor 700 also includes a stationary piece 722 that is mounted or attached to the motor 700. The stationary piece 722 defines a first lumen or hole 724 that is sized to receive the wire guide 720 therein. The stationary piece 722 also defines a second lumen or hole 726 that is sized and configured to retain a portion of the first peg 710 therein. The second lumen 726 forms a bearing surface for the first peg 710 to enable rotation of the first peg 710 within the second lumen 726 when the second gear 708 rotates. In the illustrated embodiment, the first lumen 724 has a diameter that is smaller than a diameter of the second lumen 726. As such, there is a ledge or stop 728 at the intersection of the first lumen 724 and the second lumen 726 that limits the movement of the first peg 710 within the stationary piece 722.

The hollow torque cable 709 is attached to the second peg 712 and is configured to receive the wire guide 720 therein. In use, when the motor 700 causes the shaft 702 to rotate, the shaft 702 in turn causes the first gear 706 to rotate. Rotation of the first gear 706 causes rotation of the second gear 708 and the first and the second pegs 710 and 712. Rotation of the first peg 710 causes the hollow torque cable 709 to rotate. As such when first gear 706 rotates, second gear 708 also rotates to thereby transfer rotation from a central or rotational axis in first gear 706 to a central axis in second gear 708, in other words, from an axis off center of the rotation axis of the motor 700 to the central or longitudinal axis L of the housing.

Figure 13:
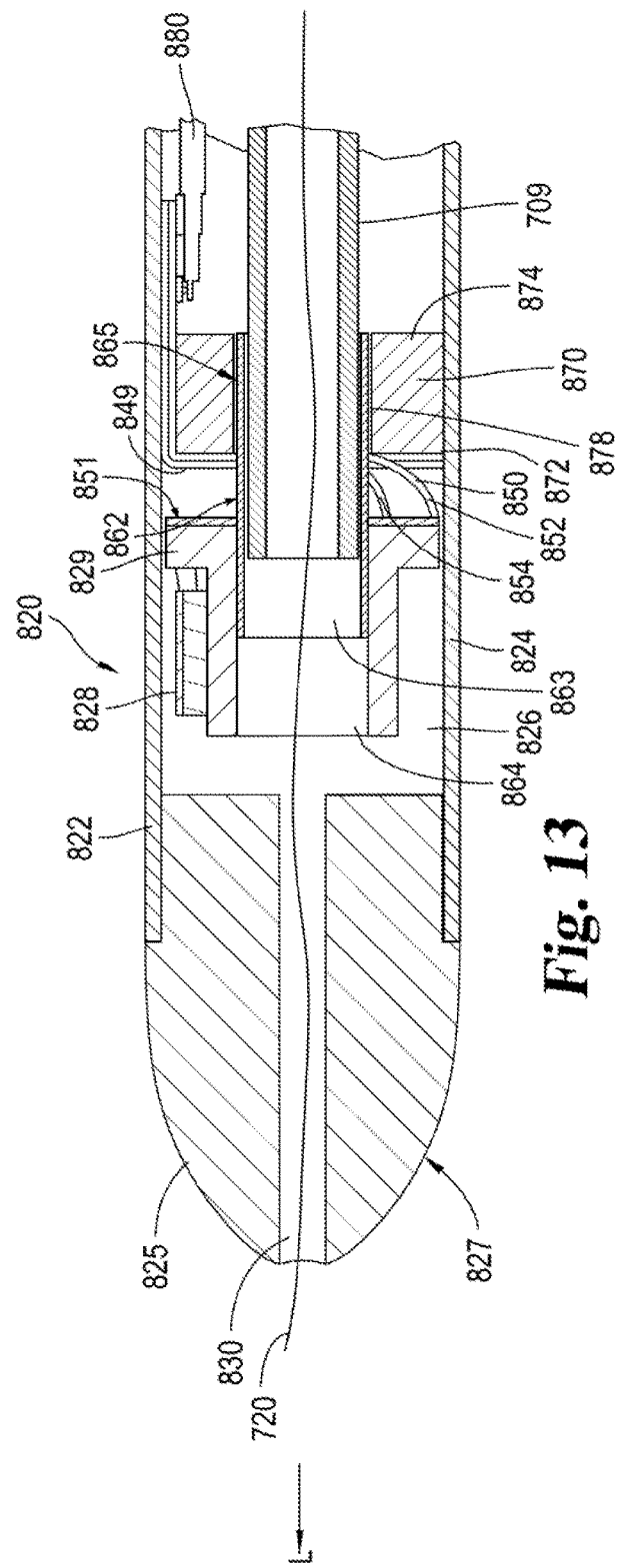
FIG. 13 is an illustrative cross-sectional view of a portion of an alternative embodiment of an ultrasound device that is connectable to either embodiment illustrated in FIG. 11 or FIG. 12.

FIG. 13 represents an alternate embodiment of a device 820 for internal ultrasound procedures that can be used with either the FIG. 11 or the FIG. 12 embodiments. This embodiment of device 820 includes similar features as device 420. Device 820 includes a catheter 822 similar to catheter 422 having a wall 824 and extending along a longitudinal axis L and a catheter tip 825 having a wall 827 and extending along the longitudinal axis L. Wall 824 has an inner surface defining an internal chamber 826, within which is included a mounting piece 829 housing a transducer 828. Wall 824 surrounds chamber 826 which is near the application end of the device 820. The application end of wall 824 is sized and configured to receive and retain a catheter tip 825. In this embodiment, a coupling medium is flushed into the chamber 826 from the handle end of the device 820.

Transducer 828 is similar to transducer 28 therefore for the sake of brevity will not be described again. Transducer 828 is operably linked to the motor 600 or 700 (positioned exterior to the catheter 822) via the torque cable 604 or 709 to permit transducer 828 to turn, pivot, or otherwise move.

A channel 830 extends from the control end to the application end of the catheter 822. Channel 830 is sized and configured to receive the wire guide 608 (or the wire guide 720). The chamber 826 is filled with a coupling medium from the control end of the catheter 822.

Device 820 includes a slip ring assembly 850 and a hollow shaft 862 similar to slip ring assembly 450 and hollow shaft 462, respectively, discussed above. Slip ring assembly 850 includes a stationary portion 849 and a rotating portion 851. The motor 600 or 700 positioned exteriorly to the wall 824 is operatively connected with the rotatable shaft 862 or the mounting piece 829 while the rotating portion 851 of the slip ring assembly 850 is operatively connected with the mounting piece 829 and the stationary portion 849 with the gear base. Slip ring assembly 850 includes brush-style rotational contacts and ring-shaped contacts as described above. Rotatable shaft 862 is a hollow cylindrical shaft having a lumen 863 extending therethrough and an outer surface 865. The lumen 863 is sized to receive and retain the application end of the hollow torque cable 604 or 709 therein. Alternatively, the outer surface 865 of the shaft 862 may be sized and configured to receive and retain the application end of the hollow torque cable 604 or 709 thereon. In either embodiment, the hollow torque cable 604 or 709 connects directly with the rotatable shaft 862.

Transducer 828 is operatively connected to the shaft 862 via the mounting piece 829 so that transducer 828 rotates in response to rotation of the shaft 862. A bore 864 similar to bore 464 extends along or substantially parallel to the rotation axis through mounting piece 829 and provides attachment to the shaft 862.

A stationary mount piece 870 includes a contact end 872 opposite a cable end 874 and a length that spans between the contact end 872 and the cable end 874. Mounted to the stationary mount piece 870 is the slip ring assembly 850. Stationary mount piece 470 includes a bore 878 that spans between the contact end 872 and the cable end 874 and is sized to receive the shaft 862 wherein the shaft 862 passes through bore 878. A bearing surface is located between the bore 878 and the shaft 862 to allow the shaft 862 to rotate with minimal friction. Also included in this embodiment is a coaxial cable 880 or other suitable conductor is electrically connected with stationary portion 849 to carry signals to the control end of the device 820.

Stationary portion 849 of the stationary mount piece 870 is similar to stationary portion 449 described above. Rotational contacts 852, 854 are similar to rotational contacts 452, 454 and are attached to the mounting piece 829. Therefore similar features for stationary portion 849 and stationary mount piece 870 will not be described again. It should be noted that for the sake of clarity, device 820 in FIG. 13 is depicted with mounting piece 829 positioned slightly away from stationary mount piece 470. For proper functioning, mounting piece 829 is positioned close enough to stationary mount piece 870 to make functional electrical connections between the stationary contacts and rotational contacts such as in an assembled configuration.

A motor such as the motor 600 or 700 is connected with the torque cable to operatively drive the shaft 862. In the embodiment in which motor 600 illustrated in FIG. 11 is connected to the device 820, there is no gear assembly needed to drive the shaft 862, instead the torque cable 604 operatively connects directly to the shaft 862 and to the motor 600. In the embodiment in which motor 700 illustrated in FIG. 12 is connected to the device 820, the gear assembly 704 drives the torque cable 709 as described above.

In the use of the term "rotation" (with respect to the rotation axis and motion about the pivot axis as well as generally), it should be understood that even though rotation often implies an angle change much greater than 360°, the devices disclosed herein may be configured in certain embodiments so that the rotational angle may rotate through angles less than 360°. In some instances the term "pivot" may be considered by some more natural than "rotate" or vice versa, but for the purposes of this application the terms "rotate" and "pivot" are used for clarity to indicate the axis about which a change in angle occurs, not the nature or magnitude of the angle change.

Many of the features described herein for the varying embodiments of device 20 can be used or interchanged with other embodiments of device 20 (device 220 and device 420) even when particular combinations of features were not specifically described, as would be understood by a person of ordinary skill in the art.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A medical ultrasound device comprising:
   a catheter having an internal chamber and a longitudinal axis extending through the internal chamber;
   a drive shaft extending substantially along the longitudinal axis;
   a non-rotating wire guide positioned along the longitudinal axis within the internal chamber;
   a transducer configured for transmitting and/or receiving ultrasound signals and operatively coupled with the drive shaft, the transducer and the drive shaft positioned within the internal chamber, wherein the transducer is rotatable about the longitudinal axis and the wire guide in response to rotation of the drive shaft;
   a torque cable positioned within the internal chamber, the torque cable offset a distance from the longitudinal axis, the torque cable operably connected to the drive shaft and a motor so that the drive shaft rotates in response to the torque cable;
   a first gear positioned within the internal chamber, said first gear operably connected to the torque cable;
   a second gear positioned within the internal chamber, said second gear operably connected to the drive shaft, wherein the second gear is configured to interact with the first gear such that the second gear is configured to rotate when the first gear rotates;
   a pusher piece positioned within the internal chamber and extending from an application end to a control end, the pusher piece defining a plurality of lumens that span a length of the pusher piece wherein one of the plurality of lumens is sized to receive the wire guide and another of the plurality of lumens is sized to receive the torque cable; and
   a stationary mount positioned within the internal chamber distal to the pusher piece, wherein the first gear is rotatably mounted to the stationary mount piece, and the second gear is rotatably mounted to the stationary mount piece.

2. The device of claim 1, wherein the first gear has a rotational axis offset from the longitudinal axis and the first gear is configured to rotate about the rotational axis; and
   the second gear is configured to rotate about the longitudinal axis when the first gear rotates.

3. The device of claim 1, further comprising:
   a mounting piece positioned within the internal chamber, the mounting piece is configured to receive the transducer and the drive shaft, wherein the mounting piece defines a lumen that aligns with the longitudinal axis and is sized to receive the wire guide such that the wire guide is non-rotatable, and the mounting piece is configured to rotate about the longitudinal axis.

4. The device of claim 3, further comprising:
   a slip ring assembly operably connected to the mounting piece and the torque cable.

5. The device of claim 4, wherein the mounting piece defines a bore that extends along the longitudinal axis, and the slip ring assembly includes said stationary mount piece configured to retain the drive shaft sized to operatively mate with the bore.

6. The device of claim 1, wherein another of the plurality of lumens of the pusher piece is sized to receive one or more transducer electrical wires operably connected to the transducer.

7. A medical ultrasound device comprising:
   an elongate housing having a longitudinal axis;
   a transducer positioned within the elongate housing, the transducer configured for transmitting and/or receiving ultrasound signals;
   a torque cable extending within the elongate housing, the torque cable set to one side of the longitudinal axis;
   a mounting piece positioned within the elongate housing and operatively coupled with the torque cable, the mounting piece also configured to receive the transducer, wherein the mounting piece defines a lumen that aligns with the longitudinal axis;
   wherein the torque cable is operably connected to the mounting piece to transmit torque to the mounting piece and is configured to rotate the mounting piece about the longitudinal axis;

a gear assembly positioned within the elongate housing, the gear assembly having a first gear interactively coupled to a second gear, wherein the first gear is rotatably mounted to a stationary mount piece within the elongate housing and the first gear is operatively connected to the torque cable, and wherein the first gear is rotatably mounted to the stationary mount piece, and the second gear is rotatably mounted to the stationary mount piece about the longitudinal axis;

a pusher piece positioned within the elongate housing and extending from an application end to a control end, the pusher piece defining a plurality of lumens that span a length of the pusher piece wherein one of the plurality of lumens is sized to receive the torque cable.

8. The device of claim 7, further comprising:

a non-rotating wire guide positioned within the housing along the longitudinal axis.

9. The device of claim 8 wherein one of the plurality of lumens is sized to receive the wire guide.

10. The device of claim 8, wherein the lumen is sized to receive the wire guide and includes an ultrasound-transmissive fluid.

11. The device of claim 8, further comprising:

a motor positioned exteriorly to the elongate housing; and a gear assembly mounted on the motor, wherein the torque cable is operably connected to the gear assembly, the torque cable further configured to receive the wire guide therein.

12. The device of claim 7, further comprising:

a motor positioned exteriorly to the elongate housing, wherein the motor is operably connected to the torque cable.

13. The device of claim 7, wherein the torque cable is offset a distance from the longitudinal axis.

14. The device of claim 7, wherein the transducer is operatively coupled with a drive shaft extending substantially along the longitudinal axis, the transducer and the drive shaft positioned within the elongate housing, wherein the transducer rotates about the longitudinal axis in response to rotation of the drive shaft.

* * * * *

UNITED STATES PATENT AND TRADEMARK OFFICE
CERTIFICATE OF CORRECTION

PATENT NO. : 11,317,892 B2
APPLICATION NO. : 15/221729
DATED : May 3, 2022
INVENTOR(S) : William J. Havel It is certified that error appears in the above-identified patent and that said Letters Patent is hereby corrected as shown below:

On the Title Page

Please change the residence of the inventor "Yun Zhou" to --Eden Prairie, MN--.

Signed and Sealed this
Twenty-sixth Day of July, 2022

Katherine Kelly Vidal
*Director of the United States Patent and Trademark Office*